(12) United States Patent
Chen et al.

(10) Patent No.: US 10,325,677 B2
(45) Date of Patent: Jun. 18, 2019

(54) APPARATUS AND COMPUTERIZED METHOD FOR OPTIMIZING OR GENERATING A SIGMA PROFILE FOR A MOLECULE

(71) Applicant: Texas Tech University System, Lubbock, TX (US)

(72) Inventors: Chau-Chyun Chen, Lubbock, TX (US); Md Rashedul Islam, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 15/310,527

(22) PCT Filed: May 11, 2015

(86) PCT No.: PCT/US2015/030108
§ 371 (c)(1),
(2) Date: Nov. 11, 2016

(87) PCT Pub. No.: WO2015/175387
PCT Pub. Date: Nov. 19, 2015

(65) Prior Publication Data
US 2017/0083688 A1 Mar. 23, 2017

Related U.S. Application Data

(60) Provisional application No. 61/991,597, filed on May 11, 2014.

(51) Int. Cl.
*G16C 60/00* (2019.01)
*G16C 10/00* (2019.01)
(Continued)

(52) U.S. Cl.
CPC ............ *G16C 10/00* (2019.02); *G06F 17/16* (2013.01); *G16C 20/30* (2019.02)

(58) Field of Classification Search
None
See application file for complete search history.

(56) References Cited

U.S. PATENT DOCUMENTS

| 7,672,826 B2 | 3/2010 | Chen et al. |
| 7,809,540 B2 | 10/2010 | Chen et al. |

(Continued)

OTHER PUBLICATIONS

Xiong et al., "An Improvement to COSMO-SAC for Predicting Thermodynamic Properties", Industrial & Engineering Chemistry Research, 2014, pp. 8265-8278.*

(Continued)

*Primary Examiner* — Kibrom K Gebresilassie
*Assistant Examiner* — Robert S Brock
(74) *Attorney, Agent, or Firm* — Daniel J. Chalker; Edwin S. Flores; Chalker Flores, LLP

(57) ABSTRACT

An apparatus and computerized method optimizes or generates a sigma profile for a molecule by receiving a sigma profile for the molecule, calculating an activity coefficient for the molecule using the sigma profile for the molecule, calculating a solubility for the molecule using the activity coefficient for the molecule, optimizing or adjusting the sigma profile for the molecule by adjusting the sigma profile using an objective function and one or more constraints, providing the sigma profile to an output device communicably coupled to a processor.

47 Claims, 17 Drawing Sheets

(51) Int. Cl.
G16C 20/30 (2019.01)
G06F 17/16 (2006.01)

(56) References Cited

U.S. PATENT DOCUMENTS

| | | | |
|---|---|---|---|
| 7,941,277 | B2 | 5/2011 | Chen |
| 8,082,136 | B2 | 12/2011 | Chen |
| 8,346,525 | B2 | 1/2013 | Chen et al. |
| 8,370,076 | B2 | 2/2013 | Chen et al. |
| 8,527,210 | B2 | 9/2013 | Chen |
| 8,660,831 | B2 | 2/2014 | Wang et al. |
| 8,666,675 | B2 | 3/2014 | Chen |
| 2009/0094006 | A1 | 4/2009 | Laidig et al. |
| 2009/0112486 | A1 | 4/2009 | Lustig |
| 2012/0095736 | A1 | 4/2012 | Wang et al. |
| 2012/0167452 | A1 | 7/2012 | Platon et al. |
| 2013/0204591 | A1 | 8/2013 | Tao et al. |

OTHER PUBLICATIONS

Song et al., "Symmetric Nonrandom Two-Liquid Segment Activity Coefficient Model for Electrolytes", Industrial & Engineering Chemistry Research, 2009, pp. 5522-5529.*

Ahlrichs, Reinhart et al. "Electronic structure calculations on workstation computers: The program system turbomole" Chemical Physics Letters, 162(3):165-169, 1989.

Bustamante, P et al. "Thermodynamic origin of the solubility profile of drugs showing one or two maxima against the polarity of aqueous and nonaqueous mixtures: niflumic acid and caffeine" Journal of pharmaceutical sciences, 91(3):874-883, 2002.

Chen, Chau-Chyun et al. "Solubility modeling with a nonrandom two-liquid segment activity coefficient model" Industrial & engineering chemistry research, 43(26):8354-8362, 2004.

Chen, Chau-Chyun "A segment-based local composition model for the gibbs energy of polymer solutions" Fluid Phase Equilibria, 83:301-312, 1993.

Delley, Bernard "An all-electron numerical method for solving the local density functional for polyatomic molecules" The Journal of chemical physics, 92(1):508-517, 1990.

Delley, B. "Analytic energy derivatives in the numerical local-density-functional approach" The Journal of chemical physics, 94(11):7245-7250, 1991.

Klamt, Andreas et al. "Cosmo-rs: a novel and efficient method for the a priori prediction of thermophysical data of liquids" Fluid Phase Equilibria, 172(1):43-72, 2000.

Klamt, Andreas et al. "Refinement and parametrization of cosmo-rs" The Journal of Physical Chemistry A, 102(26):5074-5085, 1998.

Klamt, Andreas "Conductor-like screening model for real solvents: a new approach to the quantitative calculation of solvation phenomena" The Journal of Physical Chemistry, 99(7):2224-2235, 1995.

Lin, Shiang-Tai et al. "Infinite dilution activity coefficients from ab initio solvation calculations" AIChE journal, 45(12):2606-2618, 1999.

Lin, Shiang-Tai et al. "Prediction of octanol-water partition coefficients using a group contribution solvation model" Industrial & engineering chemistry research, 38(10):4081-4091, 1999.

Lin, Shiang-Tai et al. "A priori phase equilibrium prediction from a segment contribution solvation model" Industrial & engineering chemistry research, 41(5):899-913, 2002.

Martin, A. et al. "Extended hildebrand solubility approach: methylxanthines in mixed solvents" Journal of pharmaceutical sciences, 70(10):1115-1120, 1981.

Mu, Tiancheng et al. "Performance of cosmo-rs with sigma profiles from different model chemistries" Industrial & Engineering Chemistry Research, 46(20):6612-6629, 2007.

Mullins, Eric et al. "Sigma profile database for predicting solid solubility in pure and mixed solvent mixtures for organic pharmacological compounds with cosmo-based thermodynamic methods" Industrial & Engineering Chemistry Research, 47(5):1707-1725, 2008.

Mullins, Eric et al. "Sigma-profile database for using cosmo-based thermodynamic methods" Industrial & engineering chemistry research, 45(12):4389-4415, 2006.

Paruta, AN et al. "Ethanol and methanol. solubility profiles for the xanthines in aaueous alcoholic mixtures i" Journal of Pharmaceutical Sciences, 55(10):1055-1059, 1966.

Renon, Henri et al. "Local compositions in thermodynamic excess functions for liquid mixtures" AIChE journal, 14(1):135-144, 1968.

Schmidt, Michael W. et al. "General atomic and molecular electronic structure system" Journal of Computational Chemistry, 14(11):1347-1363, 1993.

Staverman, AJ "The entropy of high polymer solutions. generalization of formulae" Recueil des Travaux Chimiques des Pays-Bas, 69(2):163-174, 1950.

Stewart, JJP "Mopac program package" Quantum Chemistry Program Exchange, (455), 1989.

Yalkowsky, SH et al. "Solubility and partitioning vi: octanol solubility and octanol—water partition coefficients" Journal of pharmaceutical sciences, 72(8):866-870, 1983.

International Search Report and Written Opinion (PCT/US2015/030108) dated Jul. 24, 2015.

\* cited by examiner

US 10,325,677 B2

APPARATUS AND COMPUTERIZED METHOD FOR OPTIMIZING OR GENERATING A SIGMA PROFILE FOR A MOLECULE

CROSS REFERENCE TO RELATED APPLICATIONS

This application claims priority to, and is the National Phase of International Application No. PCT/US2015/030108, filed on May 11, 2015, which claims the benefit under 35 U.S.C. § 119(e) of U.S. Provisional Application No. 61/991,597, filed May 11, 2014. All of which are hereby incorporated by reference in their entirety.

FIELD OF INVENTION

The present invention relates generally to the field of chemical process and product development and, more particularly, to an apparatus and computerized method for optimizing or generating a sigma profile for a molecule.

BACKGROUND ART

A priori prediction of liquid-phase non-idealities and fluid-phase equilibria has played a key role in modern chemical process and product development. A number of such predictive thermodynamic models have been widely used with either qualitative or semi-quantitative accuracy. Examples include group contribution method, i.e., Universal Quasi-Chemical Functional-Group Activity Coefficients (UNIFAC), conceptual segment approach, i.e. Non-Random Two-Liquid Segment Activity Coefficients (NRTL-SAC), and solvation thermodynamics approach, i.e. Conductor Like Screening Model for Real Solvents (COSMO-RS) and Conductor Like Screening Model for Segment Activity Coefficients (COSMO-SAC).

The group contribution method is one of the earliest of the prediction models. Among the group contribution methods, UNIFAC is the most accurate and widely used. UNIFAC defines chemical compounds and their mixtures in terms of tens of predefined chemical functional groups. Binary interaction parameters which account for inter-molecular interactions between functional groups are first optimized from millions of available experimental phase equilibrium data for thousands of molecules structured with the predefined functional groups. They are then employed to predict liquid-phase non-idealities, i.e., activity coefficients, of molecules in mixtures with the predefined functional groups. UNIFAC fails for molecules with functional groups not included in the predefined UNIFAC functional group database, and it is unable to distinguish between isomers as the same set of functional groups is present. Additionally, UNIFAC yields poor predictions for molecules with complex rigid molecular structure as the functional group additivity rule is applicable only to linear molecules.

In contrast, NRTL-SAC defines four conceptual segments each uniquely representing molecular fragments exhibiting hydrophobic, polar attractive, polar repulsive, and hydrophilic nature in molecular interactions. Like UNIFAC, binary interaction parameters for the four conceptual segments are identified from available experimental data of selected reference molecules that exhibit hydrophobicity, polarity, and hydrophilicity. Conceptual segment numbers of the concerned molecules, similar to numbers and types of functional groups in UNIFAC, are the NRTL-SAC model parameters, and they are determined from experimental data of the molecule in the presence of reference solvents. Because the conceptual segment numbers are pure component parameters, NRTL-SAC can then be used to predict phase behavior of the molecule in other solvents and solvent mixtures as long as conceptual segment numbers are known for the solvents.

Solvation thermodynamics-based models have received increased attention in recent years. Among the solvation thermodynamics-based models, conductor-like screening models (COSMO) are the most widely used. There are two different variants of COSMO, i.e., COSMO-RS and COSMO-SAC. Unlike UNIFAC and NRTL-SAC, this method determines the interaction between molecules based on a so called sigma profile, i.e., a histogram of charge density distribution over the molecular surface based on molecular structure and quantum mechanical calculations. Used together with a statistical thermodynamic expression, the resultant charge density distributions are used to compute chemical potentials of molecules in solution. The solvation thermodynamic models are advantageous over UNIFAC and NRTL-SAC when no experimental data are available. However, the COSMO models require knowledge of molecular structure and conformation to generate sigma profiles from quantum mechanical calculations, and the prediction quality of the COSMO models is qualitative in nature and often considered less reliable than that of UNIFAC and NRTL-SAC. In practice, there is a need to find a way to use the COSMO models without knowledge of molecular structure. Also, empirical treatments are proposed to correct the difference between the model predictions and the experimental data.

SUMMARY OF THE INVENTION

The present invention can be used to generate or optimize sigma profiles of any concerned molecule from conceptual segment numbers of the molecule and linear combination of sigma profiles of four reference solvents representing hydrophobic, polar attractive, polar repulsive, and hydrophilic conceptual segments. In practice, conceptual segment numbers of the molecule are identified from fitting available phase equilibrium data involving the molecule and the four reference solvents or their equivalents. This approach allows sigma profiles to be generated or optimized without knowledge of molecular structure and without use of quantum mechanical computations. The present invention achieves much improved prediction quality with the solvation thermodynamic models since the sigma profiles are optimized by fitting them against available data.

For example, the present invention provides a computerized method for optimizing a sigma profile for a molecule by providing a processor, a memory communicably coupled to the processor and an output device communicably coupled to the processor, receiving a sigma profile for the molecule, calculating an activity coefficient for the molecule using the sigma profile for the molecule, calculating a solubility for the molecule using the activity coefficient for the molecule, optimizing the sigma profile for the molecule by adjusting the sigma profile using an objective function and one or more constraints, providing the sigma profile to the output device. The method can be implemented by an apparatus or by a non-transitory computer readable medium encoded with a computer program for execution by a processor that performs the steps of the method.

The present invention also provides a computerized method for generating a sigma profile for a molecule. A processor, a memory communicably coupled to the processor and an output device communicably coupled to the processor is provided. A sigma profile is generated using a set of sigma profile vectors for a reference hydrophobicity solvent, a reference solvation solvent, a reference polarity solvent and a reference hydrophilicity solvent. An activity coefficient for the molecule is calculated using the sigma profile for the molecule. A solubility for the molecule is calculated using the activity coefficient for the molecule. A determination of whether the sigma profile has converged is made using an objective function and one or more constraints. If the sigma profile has not converged, the sigma profile for the molecule is adjusted using the objective function and the one or more constraints and the process repeats. If, however, the sigma profile has converged, the sigma profile is provided to the output device. The method can be implemented by an apparatus or by a non-transitory computer readable medium encoded with a computer program for execution by a processor that performs the steps of the method.

In addition, the present invention provides a computerized method for generating a sigma profile for a molecule. A processor, a memory communicably coupled to the processor and an output device communicably coupled to the processor is provided. A reference hydrophobicity solvent, a reference solvation solvent, a reference polarity solvent and a reference hydrophilicity solvent are selected. A set of sigma profile vectors of the reference hydrophobicity solvent, the reference solvation solvent, the reference polarity solvent and the reference hydrophilicity solvent are obtained. The sigma profile for the molecule is generated using a coefficient vector defined by:

$$p_I(\sigma)A_I = A_{ref}\begin{bmatrix} X \\ Y^- \\ Y^+ \\ Z \end{bmatrix}$$

where $A_{ref}$ is a matrix generated from the sigma profile vector of the reference hydrophobicity solvent, the reference solvation solvent, the reference polarity solvent and the reference hydrophilicity solvent, and $[X, Y^-, Y^+, Z]^T$ is a coefficient vector of hydrophobicity (X), solvation ($Y^-$), polarity ($Y^+$) and hydrophilicity (Z) at a specific temperature T.
An activity coefficient for the molecule is calculated using the sigma profile for the molecule, wherein the activity coefficient is represented by:

$$\ln\gamma_{I/S} = n_I \sum_{\sigma_m} p_I(\sigma_m)[\ln\Gamma_S(\sigma_m) - \ln\Gamma_I(\sigma_m)] + \ln\gamma_{I/S}^{SG}$$

where $\ln \gamma_{I/S}$ is a natural logarithm of the activity coefficient for the molecule, $\sigma_m$ is a charge density of a segment m, $p_I(\sigma_m)$ is the generated sigma profile for the molecule, $\ln \Gamma_I(\sigma^m)$ is a natural logarithm of a segment activity coefficient for the molecule, $\ln \Gamma_S(\sigma^m)$ is a natural logarithm of a segment activity coefficient for a mixture of the molecule and a solvent, and $\ln \gamma_{I/S}^{SG}$ is a natural logarithm of a Staverman-Guggenheim activity coefficient.
A solubility for the molecule is calculated using the activity coefficient for the molecule. A determination of whether the sigma profile has converged is made using an objective function and one or more constraints, wherein objective function and the one or more constraints can be represented by:

$$\underset{XY^-Y^+Z}{\text{minimize}} \frac{1}{n}\sum_{j}^{n}[\ln x_j^{exp} - \ln x_j^{calc}]^2$$

subject to $$p_I(\sigma) \geq 0$$

where $x_j^{exp}$ is a experimental solubility of the molecule, $\ln x_j^{calc}$ is the calculated solubility of the molecule, and $p_I(\sigma)$ is the generated sigma profile for the molecule.

If the sigma profile has not converged, the sigma profile for the molecule is adjusted using the objective function and the one or more constraints and the process repeats. If, however, the sigma profile has converged, the sigma profile is provided to the output device. The method can be implemented by an apparatus or by a non-transitory computer readable medium encoded with a computer program for execution by a processor that performs the steps of the method.

The present invention is described in detail below with reference to the accompanying drawings.

BRIEF DESCRIPTION OF THE DRAWINGS

Further benefits and advantages of the present invention will become more apparent from the following description of various embodiments that are given by way of example with reference to the accompanying drawings.

DESCRIPTION OF THE INVENTION

Figure 1:
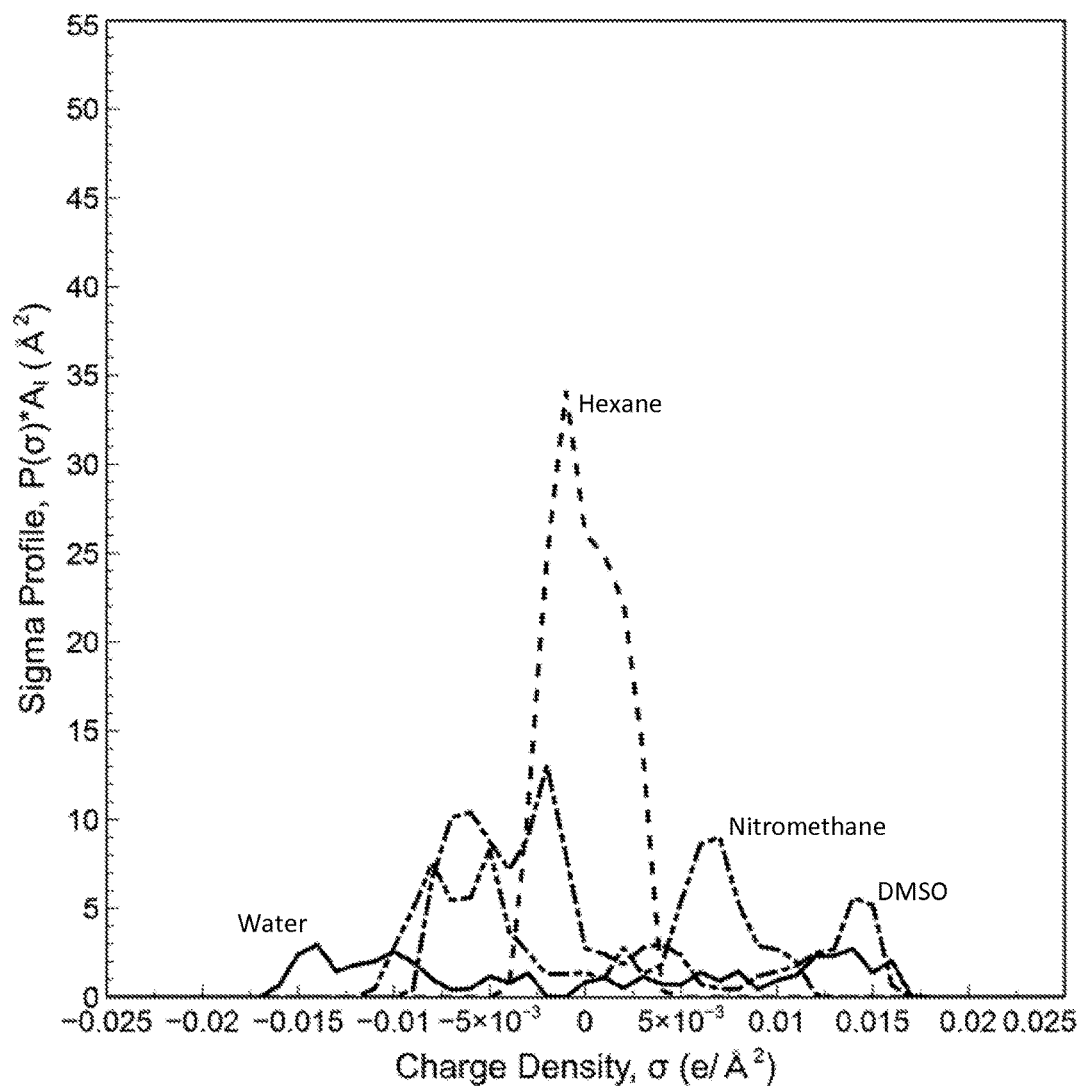
FIG. 1 is a graph showing the sigma profiles for hexane, dimethyl sulfoxide, nitromethane, and water.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

The present invention can be used to generate or optimize sigma profiles of any concerned molecule from conceptual segment numbers of the molecule and linear combination of sigma profiles of four reference solvents representing hydrophobic, polar attractive, polar repulsive, and hydrophilic conceptual segments. In practice, conceptual segment numbers of the molecule are identified from fitting available phase equilibrium data involving the molecule and the four reference solvents or their equivalents. This approach allows sigma profiles to be generated or optimized without knowledge of molecular structure and without use of quantum mechanical computations. The present invention achieves much improved prediction quality with the solvation thermodynamic models since the sigma profiles are optimized by fitting then against available data. For example, this approach has been used to generate sigma profiles and improved prediction results on solubility in pure solvents and solvent mixtures for four drug molecules: caffeine, aspirin, paracetamol, and lovastatin.

Solubility of a solid crystal in a solution is dictated by the solid-liquid equilibria (SLE). At equilibrium conditions, for a given solute, I, the solid-phase fugacity, $f_I^s$, and liquid-phase fugacity, $f_I^l$, are equal.

$$f_I^s = f_I^l \quad (1)$$

At a given temperature, T, and pressure, P, liquid-phase fugacity is the product of saturation concentration, $x_I^{sat}$, activity coefficient, $\gamma_I^{sat}$, and reference state liquid fugacity $f_I^{0l}$.

$$f_I^s = x_I^{sat} \gamma_I^{sat} f_I^{0l} \quad (2)$$

The ratio of solid-phase fugacity and reference state liquid-phase fugacity can be approximated as a function of enthalpy of fusion, $\Delta H_{fus}$, and melting temperature, $T_m$, of the solute.

$$\ln \frac{f_I^s}{f_I^{0l}} = \frac{\Delta H_{fus}}{R} \left( \frac{1}{T_m} - \frac{1}{T} \right) \quad (3)$$

From Equations 2 and 3, solubility of the solute molecule in the solvent can be expressed as $$\ln x_I^{sat} = \frac{\Delta H_{fus}}{R} \left( \frac{1}{T_m} - \frac{1}{T} \right) - \ln \gamma_I^{sat} \quad (4)$$

For a given solute with a particular polymorph, enthalpy of fusion, $\Delta H_{fus}$, and melting temperature, $T_m$, are fixed. Equation 4 indicates that at a specific temperature, T, solubility, $x_I^{sat}$, varies only with the activity coefficient, $\gamma_I^{sat}$. Heat of fusion and melting temperature are highly subjected to the polymorph of solute. Experimental data may not be available for every polymorph. Even for some solute no experimental data are reported in the literature. Experimental value of one polymorph may not reflect the solubility at all operating temperature. To avoid this problem, Equation 4 can be expressed with a solubility product constant, $K_{sp}$.

$$\ln x_I^{sat} = \ln K_{sp} - \ln \gamma_I^{sat} \quad (5)$$

From analogy to Equation 4, the logarithm of solubility product constant can be expressed as a function of temperature in Equation 6. For a specific polymorph, $A = \Delta H_{fus}/RT_m$ and $B = -\Delta H_{fus}/R$.

$$\ln K_{sp} = A + \frac{B}{T} \quad (6)$$

Solubility modeling requires accurate calculation of solute activity coefficients. As mentioned earlier, a number of activity coefficient models, i.e., UNIFAC, NRTL-SAC, and COSMOSAC, have been successfully investigated for their use in solubility modeling. An interesting fact for these three models is that they share similar theoretical formulation, as shown in Equation 7. Activity coefficients are calculated from a residual term, $\gamma_I^R$, and a combinatorial term, $\gamma_I^C$. Different models follow different approaches and assumptions to derive the residual terms and the combinatorial terms. NRTL-SAC and COSMO-SAC are to be presented briefly below.

$$\ln \gamma_I = \ln \gamma_I^R - \ln \gamma_I^C \quad (7)$$

The NRTL-SAC model originates from the segment-based concept of the polymer non-random two liquid (NRTL) activity coefficient model. To capture the "like dissolves like" phenomenon, Chen and Song represented molecules with four conceptual segments that are selected to reflect major molecular surface characteristics of intermolecular interactions: hydrophobic (X), polar attractive (Y$^-$), polar repulsive (Y$^+$), and hydrophilic (Z). Hydrophilic segments act like hydrogenbond donor, i.e., proton, or acceptor, i.e., lone-pair electrons, whereas hydrophobic segments show strong aversion to hydrogen-bond forming Polar attractive and polar repulsive segments behave like electron pair donors or acceptors. Both polar segments show weak repulsion with hydrophobic segments; polar attractive segments show certain affinity with hydrophilic segments; and polar repulsive segments show weak aversion with hydrophilic segments. Effective surface interaction characteristics of a molecule are then represented by numbers of conceptual segments of respective nature. The residual activity coefficient is expressed in Equation 8 where $r_{m,I}$ is the number of conceptual segment species m contained in component I. $\Gamma_m^{lc}$ is segment activity coefficient of conceptual segment species m in solution and $\Gamma_{m,I}^{lc}$ is segment activity coefficient of conceptual segment species m in component I.

$$\ln \gamma_I^R = \ln \gamma_I^{lc} = \sum_m r_{m,I} [\ln \Gamma_m^{lc} - \ln \Gamma_{m,I}^{lc}] \quad (8)$$

where $$m \in \{X, Y^-, Y^+, Z\}$$

For the combinatorial activity coefficient, $\gamma_I^C$, Flory-Huggins equation is adopted in Equation 9. Here $r_I$ and $\varphi_I$ are the total segment number and mole fraction of component I, respectively $$\ln \gamma_I^C = \ln \frac{\varphi_I}{x_I} + 1 - r_I \sum_J \frac{\varphi_J}{r_J} \quad (9)$$

$$r_I = \sum_m r_{m,I} \quad (9a)$$

$$\varphi_I = \frac{r_I x_I}{\sum_J r_J x_J} \quad (9b)$$

A detailed derivation of the NRTL-SAC model is available in the literature. Conceptual segment numbers for common solvent molecules and many drug molecules have been reported through regression of appropriate experimental vapor-liquid equilibrium, liquid-liquid equilibrium, and solid-liquid equilibrium data.

Thermodynamic models based on conductor like screening models are derived from solvation thermodynamics. COSMO-RS and COSMO-SAC are the two main variants. According to solvation thermodynamics, activity coefficient of a solute I is related to the solvation free energy $\Delta G^*_{I/S}{}^{sol}$. Solvation free energy is calculated from the change in energy when a solute molecule I is brought from a fixed position in an ideal gas to a fixed position in a solution S at constant temperature, T, and pressure, P. The solvation process can be described in two steps. First a discharged solute particle is inserted into a cavity of solvent. Energy required for this step is termed cavity formation free energy, $\Delta G^{*cav}$. In the following step, charges are turned on to restore electronic configuration of the solute particle. Energy required for this process is called charging free energy, $\Delta G^{*chg}$.

Cavity formation free energy depends on the shape and size of the solute molecule. Lin and Sandler proposed that $\Delta G^{*cav}$ is related to the combinatorial term of Equation 7. The Staverman-Guggenheim expression is proposed for the combinatorial term, i.e. $\gamma_I^C = \gamma_{I/S}^{SG}$.

$$\ln \gamma_{I/S}^{SG} = \ln \frac{\varphi_I}{x_I} + \frac{z}{2} q_I \ln \frac{\theta_I}{\varphi_I} + l_I - \frac{\varphi_I}{x_I} \sum_J x_J l_J \quad (10)$$

$$l_I = \frac{z}{2}(r_I - q_I) - (r_I - 1) \quad (10a)$$

$$\theta_I = \frac{x_I q_I}{\sum_J x_J q_J} \quad (10b)$$

$$\varphi_I = \frac{x_I r_I}{\sum_J x_J r_J} \quad (10c)$$

Here, $\varphi_I$ is the normalized volume fraction, $\theta_I$ is the normalized surface area fraction, Z is the co-ordination number, and $x_I$ is mole fraction of solute I. $r_I$ and $q_I$ are reported as normalized volume and surface area parameters respectively, i.e., $r_I = V_I/r$ and $q_I = A_I/q$. Here r is the standard volume parameter (66.69 Å$^3$) and q is the standard surface area parameter (79.53 Å$^2$).

Lin and Sandler further decomposed the charging free energy into two steps: ideal solvation and restoring of real fluid state. Therefore, ideal solvation free energy, $\Delta G^{*is}$, and restoring free energy, $\Delta G^{*res}$, constitute the charging free energy, $\Delta G^{*chg}$, i.e., $\Delta G^{*chg} = \Delta G^{*is} + \Delta G^{*res}$. Note that this ideal solvation free energy is the same for both the solution and pure liquid, i.e., $\Delta G^*_{I/S}{}^{is} = \Delta G^*_{I/I}{}^{is}$. The residual term in activity coefficient can be expressed by Equation 11

$$\ln \gamma_{I/S}^R = \frac{\Delta G^{*is}_{I/S} - \Delta G^{*is}_{I/I}}{RT} \quad (11)$$

In COSMO-SAC, a molecule is divided into $n_1$ number of segments having fixed surface area, $a_{eff}$ (7.5 Å$^2$). For a molecule with surface area, $A_I$, $n_I$ will be $A_I/a_{eff}$. Each segment is characterized by its charge density, σ. If $n_I(\sigma)$ is the total number of segments in a molecule having charge density, σ, the probability of finding those segments in pure liquid is $$p_I = \frac{n_I(\sigma)}{n_I} = \frac{A_I(\sigma)}{A_I} \quad (12)$$

where $A_I(\sigma)$ is the total surface area in a molecule with charge density, σ. The histogram of charge density distribution over the molecular surface is called a sigma profile. The sigma profile of a mixture is computed from the weighted average of sigma profiles of molecules in the mixture $$p_S(\sigma) = \frac{\sum_I x_I n_I p_I(\sigma)}{\sum_I x_I n_I} = \frac{\sum_I x_I A_I p_I(\sigma)}{\sum_I x_I A_I} \quad (13)$$

The sigma profile plays the pivotal role in COSMO calculations. It conveys the electronic properties of the fluid. This histogram in some ways is analogous to the functional group numbers of UNIFAC and the conceptual segment numbers of NRTL-SAC. In COSMO calculations, each segment is considered as an individual entity or ensemble. Segment activity coefficient, $\Gamma(\sigma_m)$, of a pure component or mixture conveys the interaction of segment m with charge density, $\sigma_m$, to all other n segments. Lin and Sandler expressed the restoring free energy as:

$$\frac{\Delta G_{I/S}^{*res}}{RT} = n_I \sum_{\sigma_m} p_I(\sigma_m) \ln \Gamma_S(\sigma_m) \quad (14)$$

The segment activity coefficients for pure component and mixture are expressed as $$\ln \Gamma_I(\sigma_m) = -\ln\left\{\sum_{\sigma_n} p_I(\sigma_n) \Gamma_I(\sigma_n) \exp\left[\frac{-\Delta W(\sigma_m, \sigma_n)}{RT}\right]\right\} \quad (15a)$$

$$\ln \Gamma_S(\sigma_m) = -\ln\left\{\sum_{\sigma_n} p_S(\sigma_n) \Gamma_S(\sigma_n) \exp\left[\frac{-\Delta W(\sigma_m, \sigma_n)}{RT}\right]\right\} \quad (15b)$$

where $\Delta W(\sigma_m, \sigma_n)$ is the exchange energy. This exchange energy is calculated from the following equation:

$$\Delta W(\sigma_m, \sigma_n) = \left(\frac{\alpha'}{2}\right)(\sigma_m - \sigma_n)^2 + c_{hb}\max[0, \sigma_{acc} - \sigma_{hb}]\min[0, \sigma_{don} - \sigma_{hb}] \quad (16)$$

where $\alpha'$ is the misfit energy (16466 (kcal Å$^4$)/(mol e$^2$)), $c_{hb}$ is the hydrogen bonding constant (85580 (kcal Å$^4$)/(mol e$^2$)), and $\sigma_{hb}$ is the sigma cutoff for hydrogen bonding (0.0084 e/Å$^2$). The largest and smallest values of their arguments, respectively. The activity coefficient can be calculated from Equation 17. Detailed mathematical derivation and explanation of COSMO-RS and COSMO-SAC are available in literature.

$$\ln \gamma_{I/S} = n_I \Sigma_{\sigma_m} p_I(\sigma_m)[\ln \Gamma_S(\sigma_m) - \ln \Gamma_I(\sigma_m)] + \ln \gamma_{I/S}^{SG} \quad (17)$$

Sigma profile, $p(\sigma)$, is the probability distribution of surface area having charge density $\sigma$. It is observed that ideal screening charge density for most of the molecules are in the range of −0.025 to 0.025 e/Å$^2$. Therefore, the sigma profile is often reported as histogram of segment surface over a charge density range of −0.025 to 0.025 e/Å$^2$. For convenience this interval is further with the increment of 0.001 e/Å$^2$, resulting in a vector of 51 elements.

Sigma profile generation requires use of quantum chemistry software packages. Fortunately, there exists an open-source web-based database, VT-2005 sigma profile database, for solvents and small molecules (www.design.che.vt.edu). The VT-2005 database includes sigma profiles of 1432 common compounds. This database is further supplemented by the VT-2006 database which includes an additional 32 solvents and 206 primarily larger pharmacological compounds. The reported sigma profiles in the VT databases have been calculated based on density functional theory (DFT) using DMol$^3$ module of Accelrys Materials Studio software.

There are other commercial and open-source quantum chemistry packages in addition to DMol$^3$. Examples include GAMESS, Gaussian, Jaguar, MOPAC, and TURBOMOLE. GAMESS is an open-source quantum chemistry package. Wang et al. reported a comparison study on phase equilibrium calculations of 45 binary solvents using GAMESS. Additionally, a comparison study of COSMO-RS and COSMO-SAC performance based on sigma profile generated by DMol$^3$, Gaussian, and TURBOMOLE is reported in the literature. MOPAC uses semi-empirical methods to reduce computing time. However, it is less precise than other packages.

Phase behavior prediction through COSMO calculation exclusively depends on the proper sigma profile of the molecules present in the system. As sigma profile generation requires hardcore calculation of quantum mechanics, one has to use commercial resources, such as those described above, to generate sigma profile of their molecule of interest. However, sigma profiles generated from commercial packages sometimes hold different interpretation from their experimental results. For example, the sigma profile of a molecule from a commercial package sometimes indicates higher solubility in hydrophobic solvent; whereas the actual solubility is smaller than the predicted value by several orders of magnitude. This may happen for other type of solvent. Sigma profiles calculated this way do not capture the basic nature of the segments properly: hydrophobicity, solvation, polarity, and hydrophilicity.

FIG. 1 is a graph showing the sigma profiles of four reference molecules chosen for the following analysis: hexane, dimethyl sulfoxide (DMSO), nitromethane, and water. The dashed line depicts the sigma profile for hexane. The dash-dotted line depicts the sigma profile for DMSO. The dash-dot-dotted line depicts the sigma profile for nitromethane. The solid line depicts the sigma profile for water.

Hexane, $CH_3-CH_2-CH_2-CH_2-CH_2-CH_3$, is a hydrophobic molecule. The sigma profile for hexane is observed to be narrow and inside the sigma cutoff for hydrogen bonding, i.e., $-0.0084 \leq \sigma \leq 0.0084$. In other words, it does not form a hydrogen bond with other molecules.

Water,

is hydrophilic in nature. Unlike hexane, the sigma profile for water is wide and symmetric. The two polar hydrogen atoms produce peak at $\sigma = -0.014$. On the other hand, lone-pair electrons on oxygen yield peak at $\sigma = 0.014$. The region between these two peaks is rather flat and symmetric. Therefore, water demonstrates strong hydrogen bonding interactions with other molecules.

Dimethyl sulfoxide (DMSO),

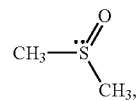

is a representative polar attractive solvent. DMSO has a highly asymmetric sigma profile. The lone-pair electrons on the sulfur atom form a peak at $\sigma = 0.014$. These electron pair donor electrostatic segments account are attractive to hydrophilic segments. In contrast, six hydrogen atoms carry counter charge. The charges on the hydrogen atoms are distributed over a large area on the negative side and form peak at $\sigma = 0.006$. However, they do not act as an electron pair acceptor.

Nitromethane,

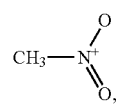

is a typical polar repulsive solvent. Nitromethane has a sigma profile almost symmetric around zero charge density, i.e., $\sigma=0$. The positive charge from the nitrogen atom yields a peak at around the sigma cutoff for hydrogen bonding of $\sigma=-0.0084$. To counterbalance this charge distribution on the negative side, surface charge segments from oxygen are distributed on the positive side with a peak at $\sigma=0.007$.

The present invention is an alternative approach for sigma profile generation that builds on the simplicity of NRTL-SAC, the predictive power of COSMO-SAC, and the confidence in actual experimental measurements. No molecular structure information nor quantum mechanical calculations are required.

Figure 2:
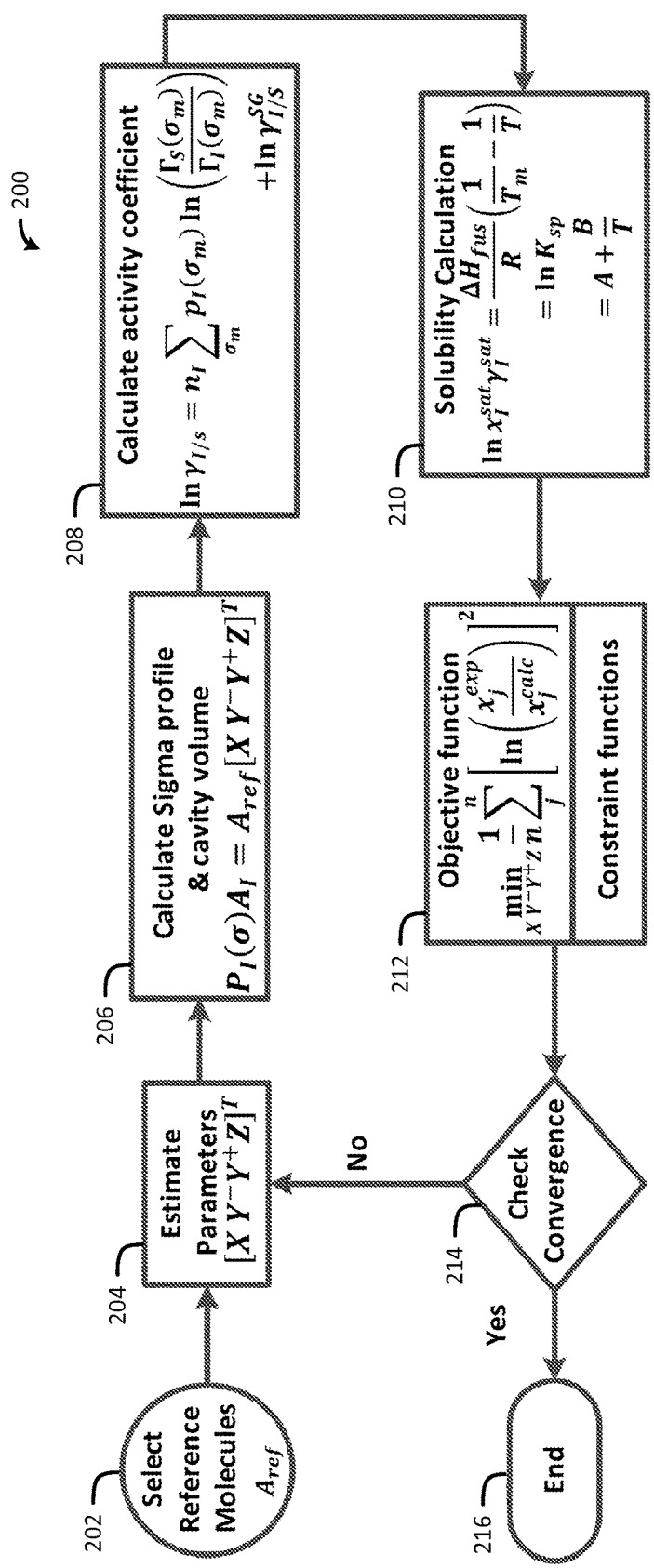
FIG. 2 is a flow chart of a method for generating sigma profiles in accordance with one embodiment of the present invention.

Now referring to FIG. 2, a flow chart of a method 200 for generating sigma profiles in accordance with one embodiment of the present invention is shown. This method for sigma profile generation follows good agreement with the experimental results. A set of reference molecules, $A_{ref}$, is selected in block 202 and an initial guess for the parameters, $[X, Y^-, Y^+, Z]^T$, is selected in block 204. A sigma profile of a molecule is generated from the linear combinations of sigma profiles of four reference solvents, each representing a particular conceptual segment (Equation 18) in block 206.

$$p_I(\sigma)A_I = A_{ref} \begin{bmatrix} X \\ Y^- \\ Y^+ \\ Z \end{bmatrix} \quad (18)$$

$A_{ref}$ matrix, with a dimension of 51×4, is generated from the sigma profile vectors of the reference molecules. The conceptual segment vector, $[X, Y^-, Y^+, Z]^T$, accounts for the respective contributions of the four conceptual segments. As a simplifying assumption for cavity volume, a spherical cavity having a surface area of $A_I$ which enshrouds the molecule is considered. The radius of the cavity, $r_{cav}$, is $(A_I/4\pi)^{1/2}$. The cavity volume thus can be calculated as $4\pi r_{cav}^3/3$. For the four conceptual segments, the reference molecules are selected based on the demonstrated nature of hydrophobicity, polarity, and hydrophilicity.

The reference solvents are selected based on exclusive nature of hydrophobicity, solvation, polarity, and hydrophilicity respectively. A list of representative solvents with their solvent characteristics are: acetic acid (complex), acetone (polar), acetonitrile (polar), anisole (hydrophobic), benzene (hydrophobic), 1-butanol (hydrophobic/hydrophilic), 2-butanol (hydrophobic/hydrophilic), n-butyl acetate (hydrophobic/polar), methyl tert-butyl ether (hydrophobic), carbon tetrachloride (hydrophobic), chlorobenzene (hydrophobic), chloroform (hydrophobic), cumene (hydrophobic), cyclohexane (hydrophobic), 1,2-dichloroethane (hydrophobic), 1,1-dichloroethylene (hydrophobic), 1,2-dichloroethylene (hydrophobic), dichloromethane (polar), 1,2-dimethoxyethane (polar), N,N-dimethylacetamide (polar), N,N-dimethylformamide (polar), dimethyl sulfoxide (polar), 1,4-dioxane (polar), ethanol (hydrophobic/hydrophilic), 2-ethoxyethanol (hydrophobic/hydrophilic), ethyl acetate (hydrophobic/polar), ethylene glycol (hydrophilic), diethyl ether (hydrophobic), ethyl formate (polar), formamide (complex), formic acid (complex), n-heptane (hydrophobic), n-hexane (hydrophobic), isobutyl acetate (polar), isopropyl acetate (polar), methanol (hydrophobic/hydrophilic), 2-methoxyethanol (hydrophobic/hydrophilic), methyl acetate (polar), 3-methyl-1-butanol (hydrophobic/hydrophilic), methyl butyl ketone (hydrophobic/polar), methylcyclohexane (polar), methyl ethyl ketone (hydrophobic/polar), methyl isobutyl ketone (hydrophobic/polar), isobutyl alcohol (hydrophobic/hydrophilic), N-methyl-2-pyrrolidone (hydrophobic), nitromethane (polar), n-pentane (hydrophobic), 1-pentanol (hydrophobic/hydrophilic), 1-propanol (hydrophobic/hydrophilic), isopropyl alcohol (hydrophobic/hydrophilic), n-propyl acetate (hydrophobic/polar), pyridine (polar), sulfolane (polar), tetrahydrofuran (polar), 1,2,3,4-tetrahydronaphthalene (hydrophobic), toluene (hydrophobic), 1,1,1-trichloroethane (hydrophobic), trichloroethylene (hydrophobic), m-xylene (hydrophobic), water (hydrophilic), triethylamine (hydrophobic/polar), and 1-octanol (hydrophobic/hydrophilic). In the following non-limiting examples, hexane, dimethyl sulfoxide, nitromethane, and water were chosen to represent hydrophobic, polar attractive, polar repulsive, and hydrophilic segments, respectively.

The resultant sigma profiles and the cavity volumes are used in the COSMO-SAC model (Equation 17) to calculate activity coefficients molecules in the system in block 208. The calculated activity coefficients are then passed to the solubility equation (Equation 5) in block 210.

$$\ln x_I^{sat}\gamma_I^{sat} = \frac{\Delta H_{fus}}{R}\left(\frac{1}{T_m} - \frac{1}{T}\right) = \ln K_{sp} = A + \frac{B}{T}$$

In the solubility calculation, enthalpy of fusion, $\Delta H_{fus}$, and melting temperature, $T_m$, are the input parameters. In case $\Delta H_{fus}$ and $T_m$ are not available or unreliable, the solubility constant, $K_{sp}$, may be included as one of the decision variables.

An objective function is formulated to minimize the error between the calculated and experimental values in Equation 19 in block 212.

$$minimize_{X,Y^-,Y^+,Z} \frac{1}{n}\sum_{j}^{n}[\ln x_j^{exp} - \ln x_j^{calc}]^2 \quad (19)$$

subject to $$p_I(\sigma) \geq 0$$

where n is number of data points, and $x_j^{exp}$ and $x_j^{calc}$ are the experimental and calculated solubility of the molecule in solvent j, respectively. The elements of the conceptual segment vector, i.e., the conceptual segment numbers, are treated as decision variables for the minimization problem.

If the sigma profile has not converged, as determined in decision block 214, the process adjusts the sigma profile in block 206 and repeats as previously described. If, however, the sigma profile has converged, as determined in decision block 214, the process ends in block 216.

For the convenience of referring to sigma profiles and cavity volumes generated from this approach, they are termed "apparent sigma profile" and "apparent cavity volume", respectively.

The sigma profile generation methodology of the present invention is illustrated with solubility modeling for four drug molecules: caffeine, aspirin, paracetamol, and lovastatin. The molecular structures of these drugs are shown below.

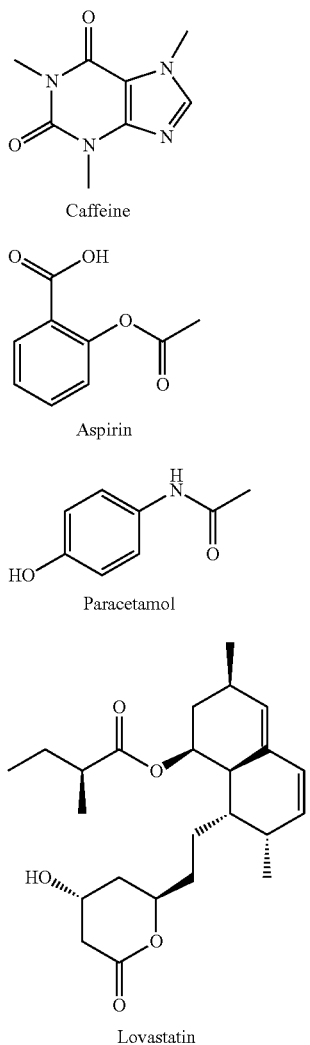

(a) Caffeine
(b) Aspirin
(c) Paracetamol
(d) Lovastatin

These drug molecules have been extensively studied in the literature with NRTL-SAC, UNIFAC, COSMO-SAC, COSMO-RS, PCSAFT, etc. The purpose of analysis below is not to show the comparison among these models. Rather, the analysis shows the apparent sigma profile, fitted against limited experimental data, offers a practical approach for correlation and prediction with COSMO-SAC and does not distort the model behavior.

To allow for meaningful determination of conceptual segment numbers for the drug molecules, solvents are included that are hydrophobic, polar attractive, polar repulsive, and hydrophilic. From the drug solubility data in the selected solvents the conceptual segment numbers, i.e., $[X, Y^-, Y^+, Z]^T$ are identified, and apparent sigma profiles for the drug molecules are generated. The apparent sigma profiles are then used with COSMO-SAC and solubility equations to predict drug solubility in other solvents and solvent mixtures. The calculated solubilities for these drug molecules are compared to their experimental values. Also included in the comparisons are the solubility predictions with drug molecule sigma profiles retrieved from the VT-2006 database.

CAFFINE: For caffeine, the melting temperature, $T_m$, is 512.15 K and enthalpy of fusion, $\Delta H_{fus}$, is 21600 kJ/kmol. These thermodynamic data result in ln $K_{sp}$=3.64 at 298.15 K. The experimental solubility data for caffeine in pure solvents are collected from the literature and reported in Table 1. Among the eight solvents, hexane, 1,4-dioxane, dimethylformamide, and water are selected to estimate the apparent sigma profile. These four solvents are selected based on their representative molecular surface interaction characteristics. The conceptual segment numbers and apparent sigma profile of caffeine are generated through regression of experimental solubility data in these four solvents. From the apparent sigma profile the caffeine solubility is then computed in all eight solvents, and they are presented in Table 1 along with the solubility prediction results from the VT-2006 sigma profile. To show that the conceptual segment numbers are a good measure of the molecular surface characteristics, the conceptual segment numbers are also estimated through regression of experimental solubility data in all eight solvents. Reported in Table 2, the conceptual segment numbers for caffeine determined with both "4 solvents" and "all solvents" are found to be very similar. Both have significant polar attractive and polar repulsive segments, low hydrophobic segments, and zero hydrophilic segments. The results suggest the conceptual segment numbers and the apparent sigma profile are relatively independent of the number of solvents used in the solubility data regression as long as the solubility data cover solvents of different molecular surface nature.

TABLE 1

Experimental and Calculated Solubility of Caffeine

| | | | Calculated Solubility | |
| --- | --- | --- | --- | --- |
| Solvent | Temp (K) | Experimental Solubility (mole frac) | VT-2006 Sigma Profile (mole frac) | Apparent Sigma Profile (mole frac) |
| hexane[a] | 298.15 | $3.94 \times 10^{-6}$ | $7.13 \times 10^{-4}$ | $4.10 \times 10^{-6}$ |
| 1,4-dioxane[a] | 298.15 | $8.20 \times 10^{-3}$ | $3.04 \times 10^{-2}$ | $6.48 \times 10^{-3}$ |
| DMF[a] | 298.15 | $1.26 \times 10^{-2}$ | $4.36 \times 10^{-2}$ | $1.45 \times 10^{-2}$ |
| water[a] | 298.15 | $2.25 \times 10^{-3}$ | $1.33 \times 10^{-3}$ | $2.24 \times 10^{-3}$ |
| 2-ethoxyethanol | 298.15 | $6.78 \times 10^{-3}$ | $2.04 \times 10^{-2}$ | $1.28 \times 10^{-2}$ |
| 1-octanol | 303.15 | $2.45 \times 10^{-3}$ | $8.69 \times 10^{-3}$ | $1.09 \times 10^{-3}$ |
| ethanol | 298.00 | $1.70 \times 10^{-3}$ | $1.82 \times 10^{-2}$ | $5.82 \times 10^{-3}$ |
| ethyl-acetate | 298.00 | $4.09 \times 10^{-3}$ | $2.31 \times 10^{-2}$ | $2.48 \times 10^{-3}$ |

[a]Solvents used for conceptual segment number estimation

TABLE 2

Conceptual Segment Numbers for Caffeine

| Conceptual Segment | Segment Numbers | |
| --- | --- | --- |
| | 4 Solvents | All Solvents |
| X | 0.109 | 0.017 |
| Y$^-$ | 1.057 | 0.869 |
| Y$^+$ | 1.255 | 1.440 |
| Z | 0 | 0 |

Figure 3:
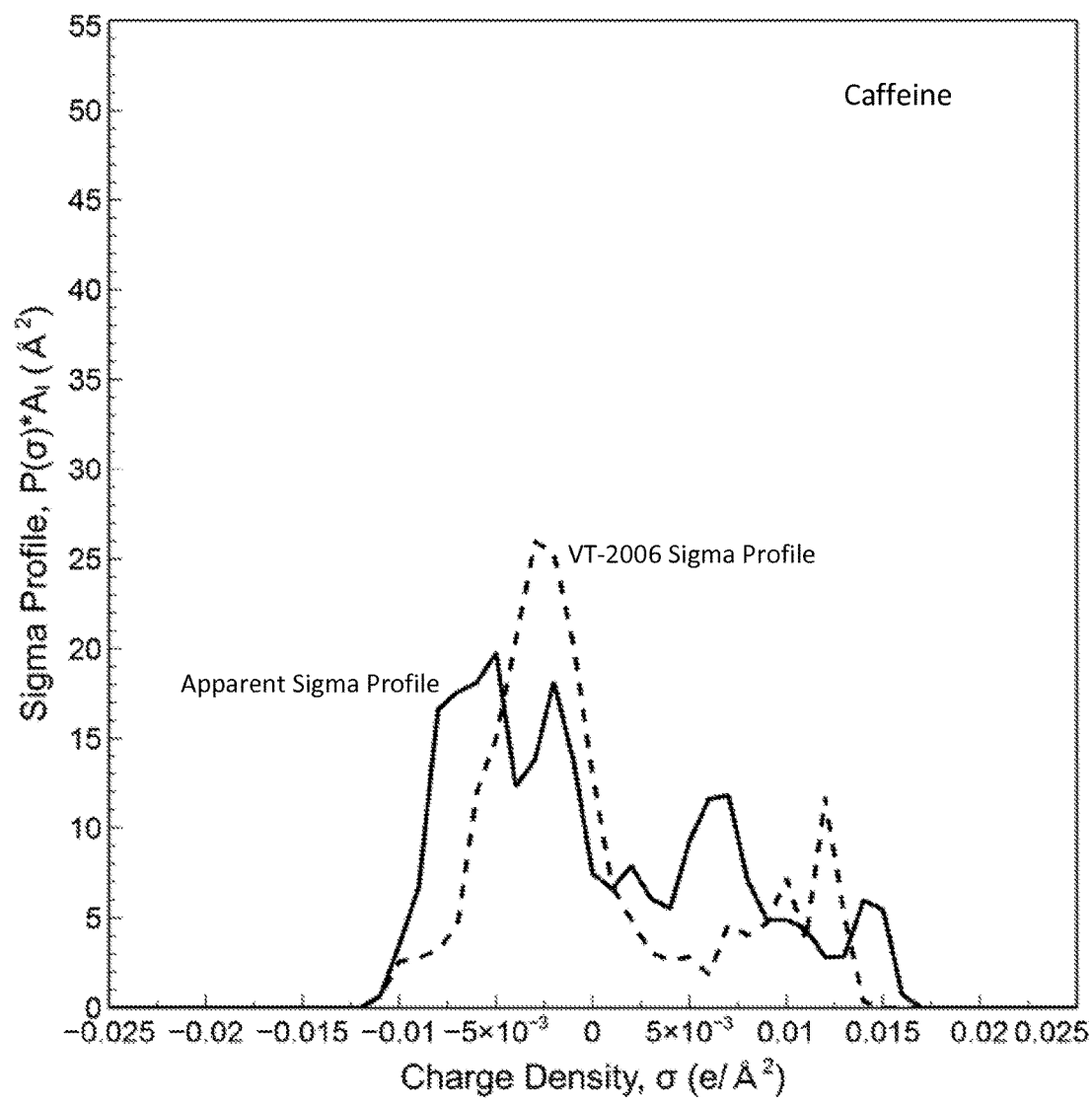
FIG. 3 is a graph showing the apparent sigma profile estimated with four solvents along with the VT-2006 sigma profile for caffeine in accordance with one embodiment of the present invention.

FIG. 3 shows the apparent sigma profile estimated with four solvents along with the VT-2006 sigma profile for caffeine. The VT-2006 sigma profile for caffeine is the dashed line. The apparent sigma profile for caffeine is the solid line. The apparent sigma profile differs significantly from the VT-2006 sigma profile. The VT-2006 sigma profile for caffeine, similar to that of hexane shown in FIG. 1, shows level of hydrophobic segments significantly higher than that of the apparent sigma profile. The apparent cavity volume of the caffeine molecule calculated from the apparent sigma profile is 363.22 Å$^3$. In comparison, the VT-2006 database reported the cavity volume of the caffeine molecule as 219.23 Å$^3$. It should be noted that the apparent cavity volume is calculated with the simplifying assumption of a spherical cavity.

Table 3 reports the model errors with the two apparent sigma profiles identified with "4 solvents" and "all solvents" and the VT-2006 sigma profile in terms of root-mean-square error (RMSE) in logarithm of solubility, i.e., $[(1/N)\Sigma_i^N(\ln x_i^{Exp} - \ln x_i^{Calc})^2]^{1/2}$.

TABLE 3

RMSE in Logarithm of Solubility of Caffeine in Eight Pure Solvents

| VT-2006 | Apparent Sigma Profile | |
|---|---|---|
| Sigma Profile | 4 Solvents | All Solvents |
| 2.29 | 0.60 | 0.57 |

Figure 4:
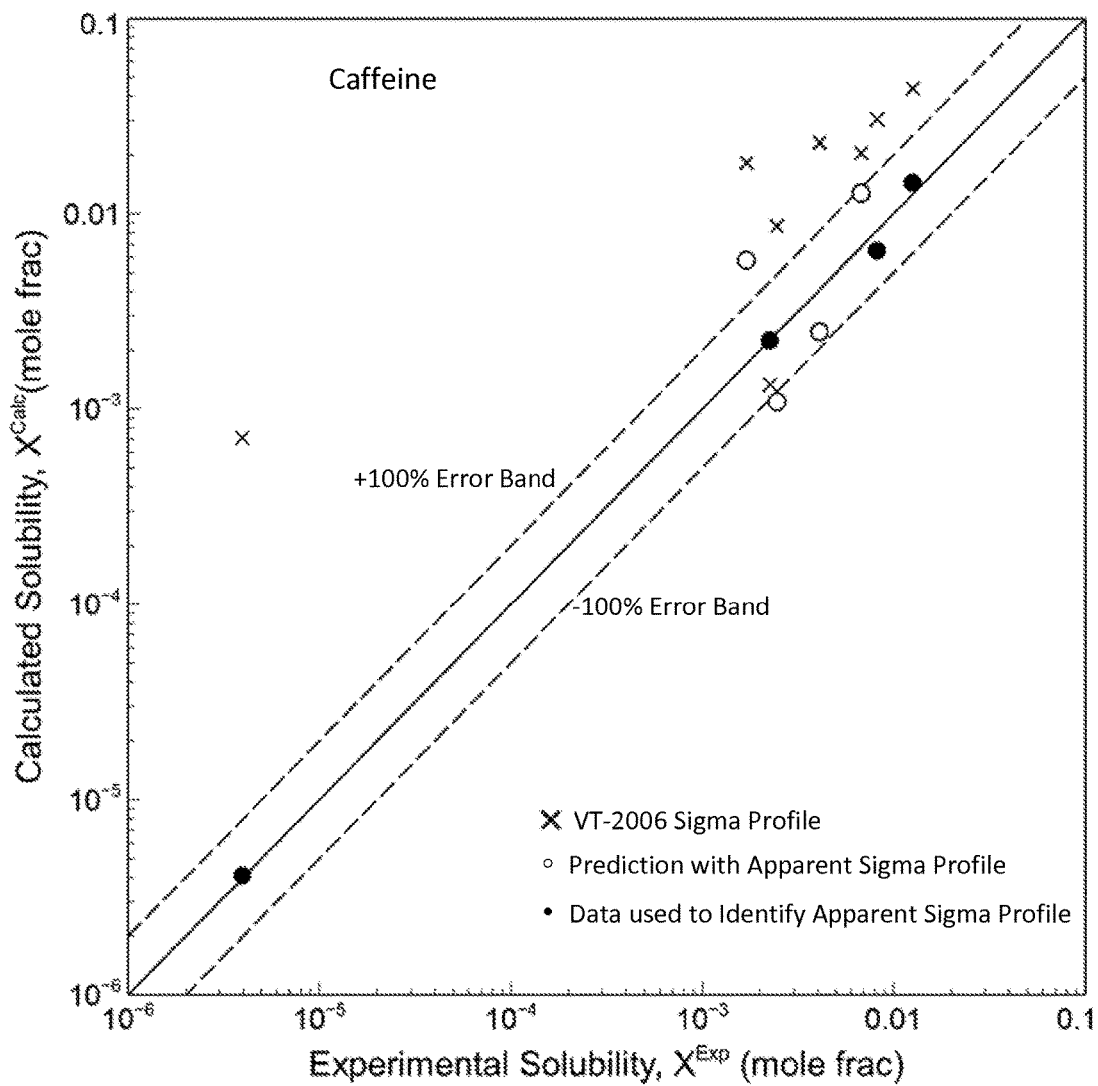
FIG. 4 is a graph showing the parity plot comparing the experimental and calculated solubilities for caffeine in accordance with one embodiment of the present invention.

FIG. 4 shows the parity plot comparing the experimental and calculated solubilities: prediction with VT-2006 sigma profile (×), prediction with apparent sigma profile (○), data used to identify apparent sigma profile (•), ±100% error band (dashed lines). COSMO-SAC with the VT-2006 sigma profile over predicts caffeine solubility in all solvents except water. This reflects the fact that the VT-2006 sigma profile suggests significant hydrophobic segments similar to that of hexane. However, this is not consistent with the experimental observation as the caffeine solubility data show very low solubility in hexane. In contrast, the apparent sigma profile suggests low hydrophobic segments, zero hydrophilic segments, and significant polar attractive and polar repulsive segments (Table 2). COSMO-SAC with the apparent sigma profile calculates caffeine solubility in the eight solvents much closer to the experimental data than those predicted with the VT-2006 sigma profile.

ASPIRIN: For, aspirin, the melting temperature and the enthalpy of fusion are 408.15 K and 25,600 kJ/kmol, respectively. ln Ksp is calculated as −2.78 at 298.15 K from these thermodynamic data.

Figure 5:
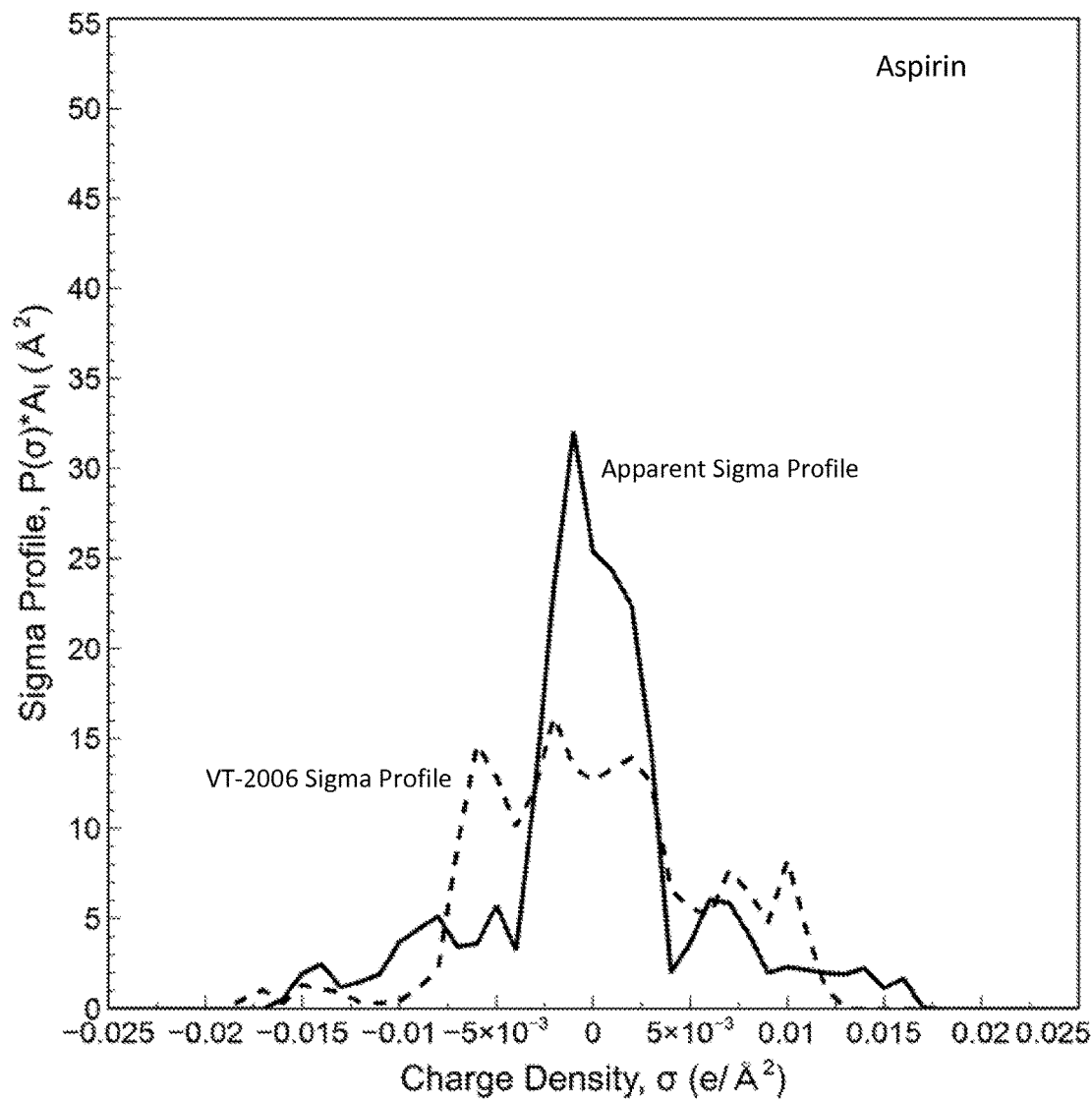
FIG. 5 is a graph showing the apparent sigma profile of aspirin together with the VT-2006 sigma profile in accordance with one embodiment of the present invention.

Frank et al. reported experimental solubility of aspirin in 23 pure solvents at 298.15 K. (See Table 4). K.36 (See Table 4). To generate the apparent sigma profile for aspirin, the experimental solubility data of aspirin is regressed in four solvents, i.e., methanol, acetone, acetic acid, and cyclohexane. FIG. 5 shows the apparent sigma profile of aspirin together with the VT-2006 sigma profile: prediction with VT-2006 sigma profile (×), prediction with apparent sigma profile (○), data used to identify apparent sigma profile (•), ±100% error band (dashed lines). In contrast to the case of caffeine, the apparent sigma profile for aspirin contains hydrophobic segments significantly higher than that of the VT-2006 sigma profile. To examine the effects of other solvents, the apparent sigma profile is also estimated using 20 solvents with three chlorohydrocarbon solvents excluded. The reason for excluding the three chlorohydrocarbon solvents will be explained later. The conceptual segment numbers for aspirin estimated from two sets of solvents are presented in Table 5. Both show zero or low polar attractive segments and significant hydrophobic, polar repulsive, and hydrophilic segments. The apparent cavity volume of aspirin molecule is calculated to be 328.15 Å$^3$. In comparison, the VT-2006 database reported the cavity volume of aspirin molecule as 206.19 Å$^3$.

Solubility calculation results with the apparent sigma profile calculated with four solvents and the VT-2006 sigma profile are reported in Table 4.

TABLE 4

Experimental and Calculated Solubility of Aspirin at 298.15 K

| | | Calculated Solubility | |
|---|---|---|---|
| Solvent | Experimental Solubility (mole frac) | VT-2006 Sigma Profile (mole frac) | Apparent Sigma Profile (mole frac) |
| methanol[a] | 8.05 × 10$^{-2}$ | 1.88 × 10$^{-1}$ | 6.40 × 10$^{-2}$ |
| acetone[a] | 1.16 × 10$^{-1}$ | 3.02 × 10$^{-1}$ | 1.14 × 10$^{-1}$ |
| acetic acid[a] | 4.35 × 10$^{-2}$ | 5.69 × 10$^{-2}$ | 4.86 × 10$^{-2}$ |
| cyclohexane[a] | 2.34 × 10$^{-5}$ | 8.26 × 10$^{-4}$ | 2.31 × 10$^{-5}$ |
| ethanol | 6.01 × 10$^{-2}$ | 2.40 × 10$^{-1}$ | 7.92 × 10$^{-2}$ |
| 1,4-dioxane | 1.03 × 10$^{-1}$ | 2.67 × 10$^{-1}$ | 8.40 × 10$^{-2}$ |
| methyl ethyl ketone | 5.18 × 10$^{-2}$ | 3.08 × 10$^{-1}$ | 1.17 × 10$^{-1}$ |
| diacetone alcohol | 6.69 × 10$^{-2}$ | 3.88 × 10$^{-1}$ | 1.68 × 10$^{-1}$ |
| isopropanol | 3.57 × 10$^{-2}$ | 2.53 × 10$^{-1}$ | 8.05 × 10$^{-2}$ |
| isoamyl alcohol | 5.16 × 10$^{-2}$ | 1.58 × 10$^{-1}$ | 4.37 × 10$^{-2}$ |
| 2-ethyl hexanol | 7.43 × 10$^{-2}$ | 1.65 × 10$^{-1}$ | 4.40 × 10$^{-2}$ |
| propylene glycol | 4.01 × 10$^{-2}$ | 2.15 × 10$^{-1}$ | 4.64 × 10$^{-2}$ |
| chloroform | 4.06 × 10$^{-2}$ | 9.68 × 10$^{-2}$ | 6.16 × 10$^{-2}$ |
| diethyl ether | 2.12 × 10$^{-2}$ | 2.23 × 10$^{-1}$ | 5.05 × 10$^{-2}$ |
| methyl benzoate | 3.05 × 10$^{-2}$ | 9.56 × 10$^{-2}$ | 4.11 × 10$^{-3}$ |
| ethyl butyrate | 2.62 × 10$^{-2}$ | 1.59 × 10$^{-1}$ | 1.27 × 10$^{-2}$ |
| diethyl maleate | 3.83 × 10$^{-2}$ | 1.28 × 10$^{-1}$ | 9.13 × 10$^{-3}$ |
| diethyl malonate | 3.57 × 10$^{-2}$ | 2.71 × 10$^{-1}$ | 2.59 × 10$^{-2}$ |
| acetal | 2.66 × 10$^{-2}$ | 1.75 × 10$^{-1}$ | 2.43 × 10$^{-2}$ |
| 1-octanol | 2.19 × 10$^{-2}$ | 1.78 × 10$^{-1}$ | 3.46 × 10$^{-2}$ |
| tetrachloroethylene | 2.77 × 10$^{-2}$ | 2.15 × 10$^{-3}$ | 5.73 × 10$^{-5}$ |
| 1,2-dichloroethane | 1.67 × 10$^{-2}$ | 3.19 × 10$^{-2}$ | 5.32 × 10$^{-4}$ |
| 1,1,1-trichloroethane | 3.71 × 10$^{-3}$ | 1.10 × 10$^{-2}$ | 3.20 × 10$^{-4}$ |

[a]Solvents used for conceptual segment number estimation

TABLE 5

Conceptual Segment Numbers for Aspirin

| Conceptual | Segment Numbers | |
|---|---|---|
| Segment | 4 Solvents | All Solvents[b] |
| X | 0.917 | 0.532 |
| Y$^-$ | 0 | 0.032 |
| Y$^+$ | 0.568 | 1.086 |
| Z | 0.823 | 0.559 |

[b]With tetrachloroethylene, 1,2-dichloroethane, and 1,1,1-trichloroethane excluded The VT-2006 sigma profile over predicts aspirin solubility in all solvents except tetrachloroethylene. The apparent sigma profile yields very good results of aspirin solubility in alcohols, ketones, carboxylic acids, ethers, esters, acetals, and chloroform. However, it is found that the apparent sigma profile grossly under-predicts the aspirin solubility in the three chlorohydrocarbon solvents: tetrachloroethylene, 1,2-dichloroethane, and 1,1,1,-trichloroethane. It is not obvious to us why the model predicts aspirin solubility well for chloroform but rather poorly for the other three chlorohydrocarbon solvents. The poor predictions for the three chlorohydrocarbon solvents remain even if the solubility data in these three solvents are used to generate the conceptual segment numbers and the apparent sigma profile. The model errors in terms of root-mean-square error in logarithm of solubility for the two different apparent sigma profiles identified with "4 solvents" and "all solvents" and the VT-2006 sigma profile are reported in Table 6.

TABLE 6

RMSE in Logarithm of Solubility of Aspirin in 23 Pure Solvents

| VT-2006 Sigma Profile | Apparent Sigma Profile | |
|---|---|---|
| | 4 Solvents | All Solvents |
| 1.68 | 1.70 | 1.31 |
| 1.68[a] | 0.73[a] | 0.57[a] |

Figure 6:
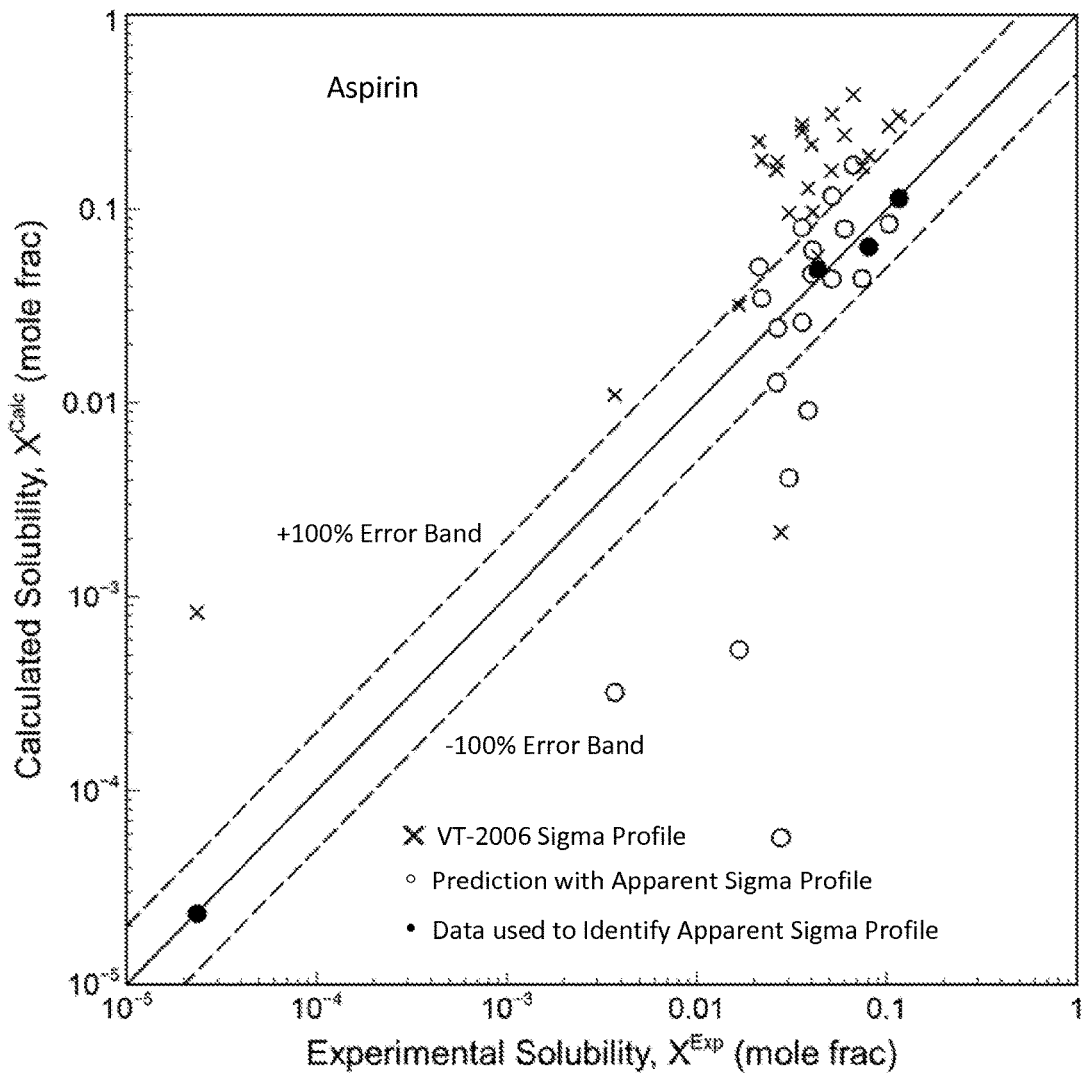
FIG. 6 is a graph showing the parity plot comparing the experimental and calculated solubilities for aspirin in accordance with one embodiment of the present invention.

[a]With tetrachloroethylene, 1,2-dichloroethane, and 1,1,1-trichloroethane excluded Additionally a parity plot of experimental and calculated solubility is presented in FIG. 6: prediction with VT-2006 sigma profile (×), prediction with apparent sigma profile (○), data used to identify apparent sigma profile (•), ±100% error band (dashed lines).

PARACETAMOL: For paracetamol, the melting temperature and the enthalpy of fusion are reported as 441.2 K and 26000 kJ/kmol, respectively. These reported thermodynamic constants result in $\ln K_{sp}=-3.40$ at 298.15 K and $\ln K_{sp}=-3.23$ at 303.15 K.

Granberg and Rasmuson reported the experimethal solubility of paracetamol in 26 pure solvents at 303.15 K. The conceptual segment numbers for paracetamol are estimated using the experimental data of four solvents, i.e., water, acetone, dimethyl sulfoxide, and toluene. The apparent sigma profile calculated from the conceptual segment numbers is then used to estimate the solubility of paracetamol in all 26 solvents (Table 7). To examine the effects of other solvents, the conceptual segment numbers are further estimated using the entire set of 26 solvents. The conceptual segment numbers for paracetamol estimated from the two sets of solvents are reported in Table 8. The two sets of conceptual segment numbers are found to be consistent, and both suggest substantial hydrophobicity and high hydrophilicity for paracetamol.

TABLE 7

Experimental and Calculated Solubility of Paracetamol at 303.15 K

| | | Calculated Solubility | |
|---|---|---|---|
| Solvent | Experimental Solubility (mole frac) | VT-2006 Sigma Profile (mole frac) | Apparent Sigma Profile (mole frac) |
| water[a] | $2.07 \times 10^{-3}$ | $3.67 \times 10^{-3}$ | $2.10 \times 10^{-3}$ |
| acetone[a] | $4.11 \times 10^{-2}$ | $2.01 \times 10^{-1}$ | $5.16 \times 10^{-2}$ |
| Dimethyl sulfoxide[a] | $3.69 \times 10^{-1}$ | $4.24 \times 10^{-1}$ | $2.28 \times 10^{-1}$ |
| toluene[a] | $2.07 \times 10^{-4}$ | $2.19 \times 10^{-4}$ | $1.97 \times 10^{-4}$ |
| methanol | $7.30 \times 10^{-2}$ | $1.36 \times 10^{-1}$ | $5.83 \times 10^{-2}$ |
| ethanol | $6.62 \times 10^{-2}$ | $1.60 \times 10^{-1}$ | $6.64 \times 10^{-2}$ |
| ethylene glycol | $5.59 \times 10^{-2}$ | $6.40 \times 10^{-2}$ | $2.80 \times 10^{-2}$ |
| 1-propanol | $5.01 \times 10^{-2}$ | $1.39 \times 10^{-1}$ | $5.95 \times 10^{-2}$ |
| 2-propanol | $5.09 \times 10^{-2}$ | $1.57 \times 10^{-1}$ | $6.67 \times 10^{-2}$ |
| 1-butanol | $4.39 \times 10^{-2}$ | $1.28 \times 10^{-1}$ | $5.56 \times 10^{-2}$ |
| 1-pentanol | $3.80 \times 10^{-2}$ | $1.08 \times 10^{-1}$ | $4.95 \times 10^{-2}$ |
| 1-hexanol | $3.25 \times 10^{-2}$ | $9.89 \times 10^{-2}$ | $4.66 \times 10^{-2}$ |
| 1-heptanol | $2.80 \times 10^{-2}$ | $8.48 \times 10^{-2}$ | $4.20 \times 10^{-2}$ |
| 1-octanol | $2.31 \times 10^{-2}$ | $7.86 \times 10^{-2}$ | $4.02 \times 10^{-2}$ |
| methyl ethyl ketone | $3.23 \times 10^{-2}$ | $1.95 \times 10^{-1}$ | $5.53 \times 10^{-2}$ |
| methyl isobutyl ketone | $1.17 \times 10^{-2}$ | $1.18 \times 10^{-1}$ | $2.97 \times 10^{-2}$ |
| tetrahydrofuran | $6.90 \times 10^{-2}$ | $2.27 \times 10^{-1}$ | $1.09 \times 10^{-1}$ |
| 1,4-dioxane | $9.86 \times 10^{-3}$ | $1.57 \times 10^{-1}$ | $3.20 \times 10^{-2}$ |
| ethyl acetate | $6.21 \times 10^{-3}$ | $8.56 \times 10^{-2}$ | $1.33 \times 10^{-2}$ |
| acetonitrile | $8.84 \times 10^{-3}$ | $6.40 \times 10^{-2}$ | $6.09 \times 10^{-3}$ |
| diethylamine | $3.89 \times 10^{-1}$ | $2.62 \times 10^{-1}$ | $2.04 \times 10^{-1}$ |
| N,N-dimethylformamide | $3.29 \times 10^{-1}$ | $3.60 \times 10^{-1}$ | $1.84 \times 10^{-1}$ |
| acetic acid | $3.18 \times 10^{-2}$ | $6.23 \times 10^{-2}$ | $6.85 \times 10^{-2}$ |
| dichloromethane | $1.80 \times 10^{-4}$ | $4.90 \times 10^{-3}$ | $2.22 \times 10^{-3}$ |
| chloroform | $1.21 \times 10^{-3}$ | $1.97 \times 10^{-2}$ | $2.15 \times 10^{-2}$ |
| carbon tetrachloride | $9.05 \times 10^{-4}$ | $2.66 \times 10^{-5}$ | $6.04 \times 10^{-5}$ |

[a]Solvents used for conceptual segment number estimation

TABLE 8

Conceptual Segment Numbers for Paracetamol

| Conceptual Segment | Segment Numbers | |
|---|---|---|
| | 4 Solvents | All Solvents |
| X | 0.488 | 0.338 |
| Y⁻ | 0 | 0 |
| Y⁺ | 0.153 | 0 |
| Z | 0.868 | 0.820 |

Figure 7:
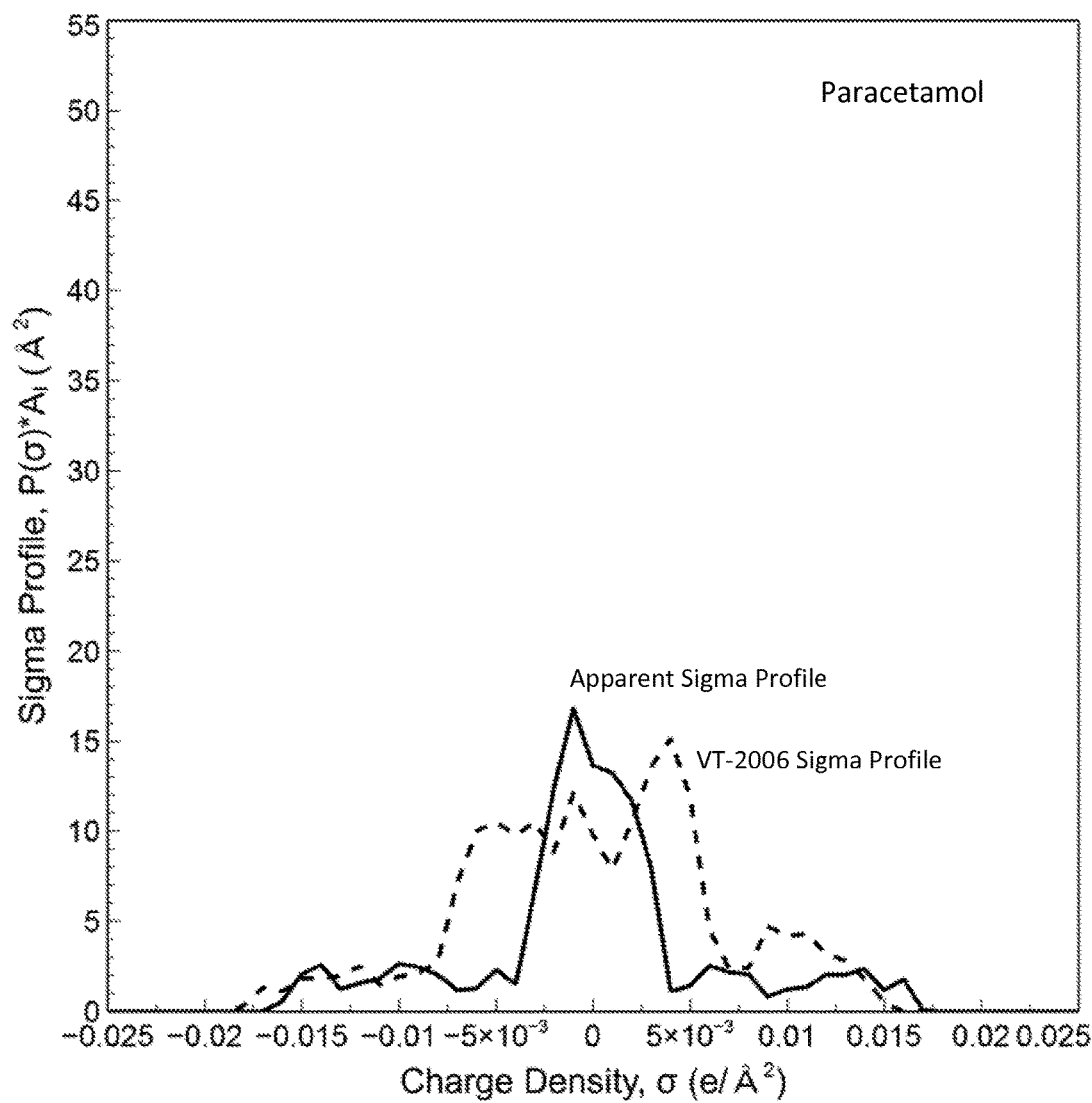
FIG. 7 is a graph showing the apparent sigma profile of paracetamol together with the VT-2006 sigma profile in accordance with one embodiment of the present invention.

The apparent sigma profile, estimated from four solvents, is shown in FIG. 7 together with the VT-2006 sigma profile for paracetamol: VT-2006 (dashed line) and apparent sigma profile (solid line). The apparent cavity volume of paracetamol is calculated as 135.82 Å³, whereas the VT-2006 cavity volume of paracetamol is 183.80 Å³.

Figure 8:
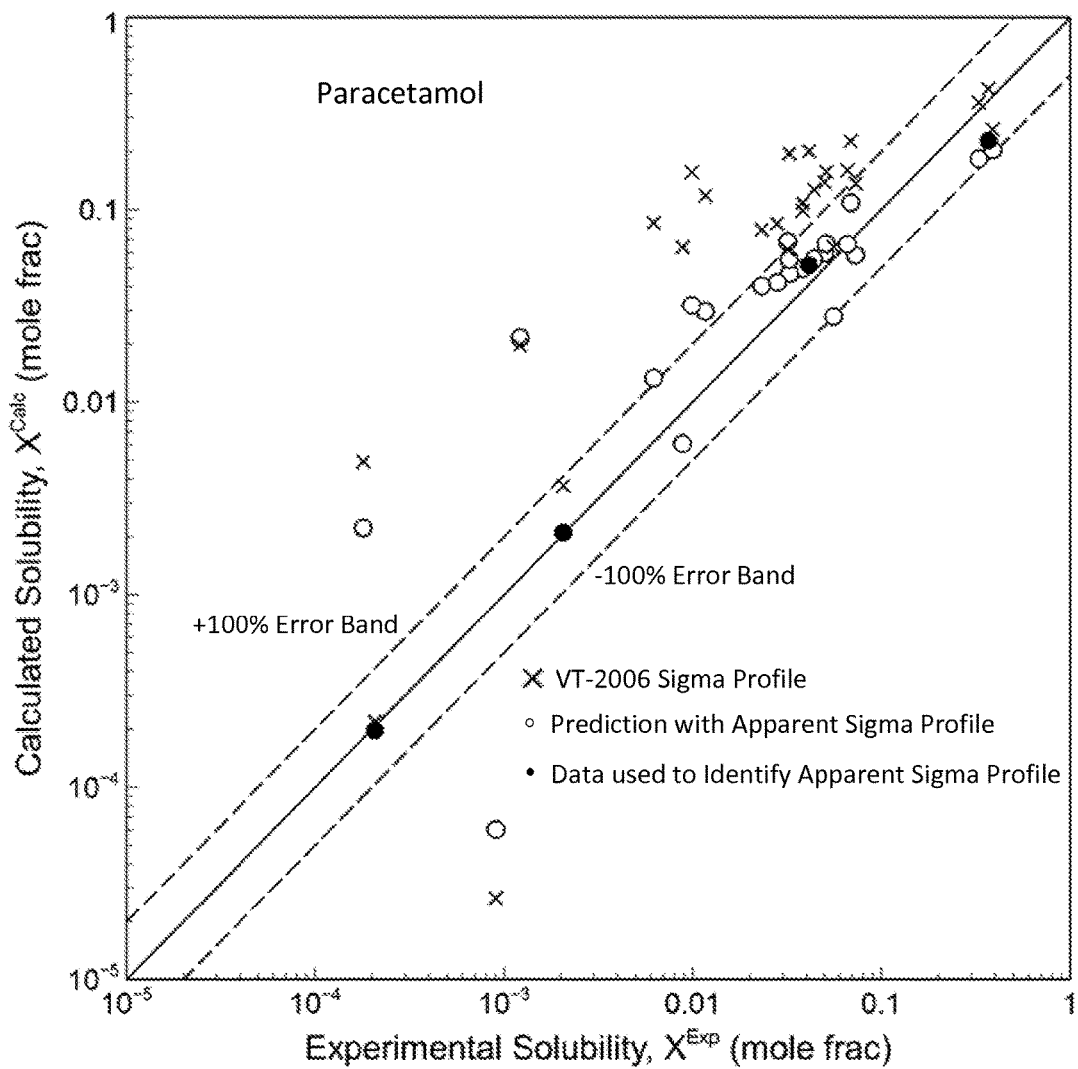
FIG. 8 is a graph showing the parity plot comparing the experimental and calculated solubilities for paracetamol in accordance with one embodiment of the present invention.

Table 7 shows the paracetamol solubility in the 26 solvents as calculated with the apparent sigma profile and the VT-2006 sigma profile. FIG. 8 shows the parity plot for the experimental and calculated solubility: prediction with VT-2006 sigma profile (×), prediction with apparent sigma profile (○), data used to identify apparent sigma profile (•), ±100% error band (dashed line). Table 9 summarizes the model errors for paracetamol for the two apparent sigma profiles and the VT-2006 sigma profile in terms of root-meansquare error in logarithm of solubility.

TABLE 9

RMSE in Logarithm of Solubility of Paracetamol in 26 Pure Solvents

| VT-2006 Sigma Profile | Apparent Sigma Profile | |
|---|---|---|
| | 4 Solvents | All Solvents |
| 1.67 | 1.04 | 0.95 |

The model error from the VT-2006 sigma profile is significantly larger than those of the apparent sigma profiles. The VT-2006 sigma profile over predicts paracetamol solubility in all solvents except for diethylamine and carbon tetrachloride. For example, the predictions for alcohol solvents are around two to three times higher than the experimental data. The over predictions for paracetamol solubility in ketone and ester solvents are even more pronounced than those for the alcohol solvents. Furthermore, the VT-2006 sigma profile gives very poor predictions for the three chlorohydrocarbon solvents. It over predicts the paracetamol solubility in dichloromethane and chloroform by 27 and 16 fold, respectively, and under predicts the solubility in carbon tetrachloride by a factor of 34.

Paracetamol solubility model results with the apparent sigma profiles are fairly close to the experimental data for alcohol, ketone, amide, amine, carboxylic acid, and ester solvents. However, like the VT-2006 sigma profile, the apparent sigma profile performs poorly with the paracetamol solubility in the chlorohydrocarbon solvents. Although there is a slight improvement over the VT-2006 sigma profile predictions, the apparent sigma profile overestimates the paracetamol solubility in dichloromethane and chloroform by a factor of 12 and 18, respectively, and underestimates the solubility in carbon tetrachloride by a factor of 15. It is worth noting that poor solubility predictions are observed in the chlorohydrocarbon solvents with both aspirin molecule and paracetamol molecule.

Paracetamol solubility is further predicted in four binary solvents for which solubility predictions have been done previously with NRTL-SAC at 298.15 K. These four binary solvents include methanol-water, acetone-water, acetone-toluene, and methanol-ethyl acetate binaries. Note that, among the solvents, water is hydrophilic, methanol is partly hydrophilic and partly hydrophobic, acetone is polar, toluene is hydrophobic, and ethyl acetate is partly hydrophobic and partly polar. The prediction results are presented with the apparent sigma profile determined with four solvents.

Figure 9:
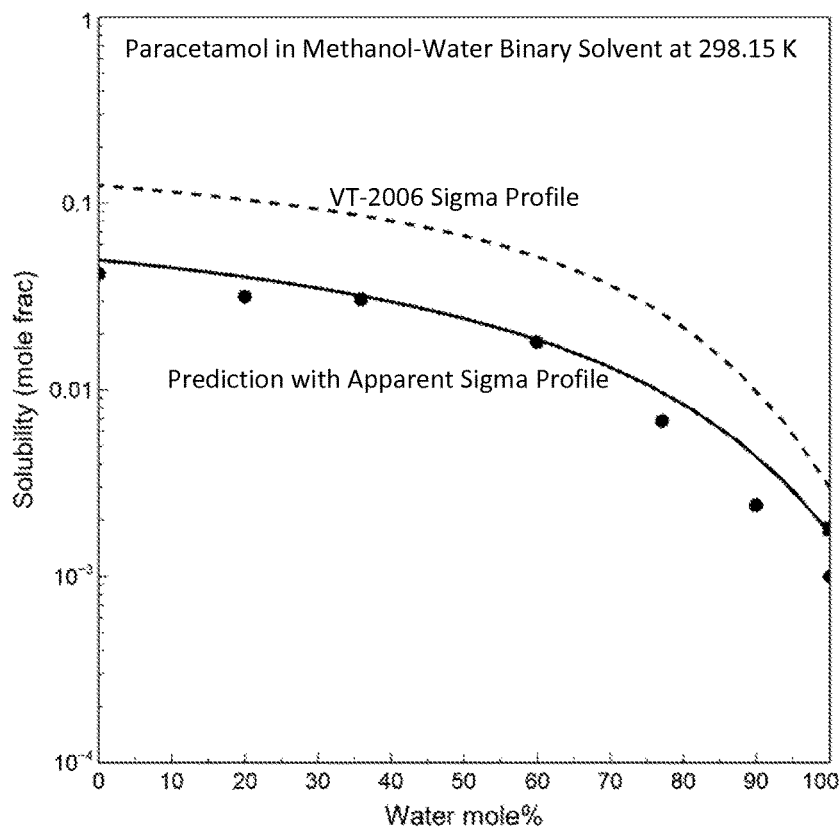
FIG. 9 is a graph showing prediction results for paracetamol solubility in methanol-water binary at 298.15 K with both the apparent sigma profile and the VT-2006 sigma profile in accordance with one embodiment of the present invention.

FIG. 9 shows prediction results for paracetamol solubility in methanol-water binary at 298.15 K with the apparent sigma profile (solid line), the VT-2006 sigma profile (dashed line), experimental data (•), and experimental data (■). The VT-2006 sigma profile overpredicts the solubility of paracetamol in this binary system. However, the prediction trend seems to be consistent with that of the experimental one. In contrast, the apparent sigma profile predicted paracetamol solubility with excellent accuracy.

Figure 10:
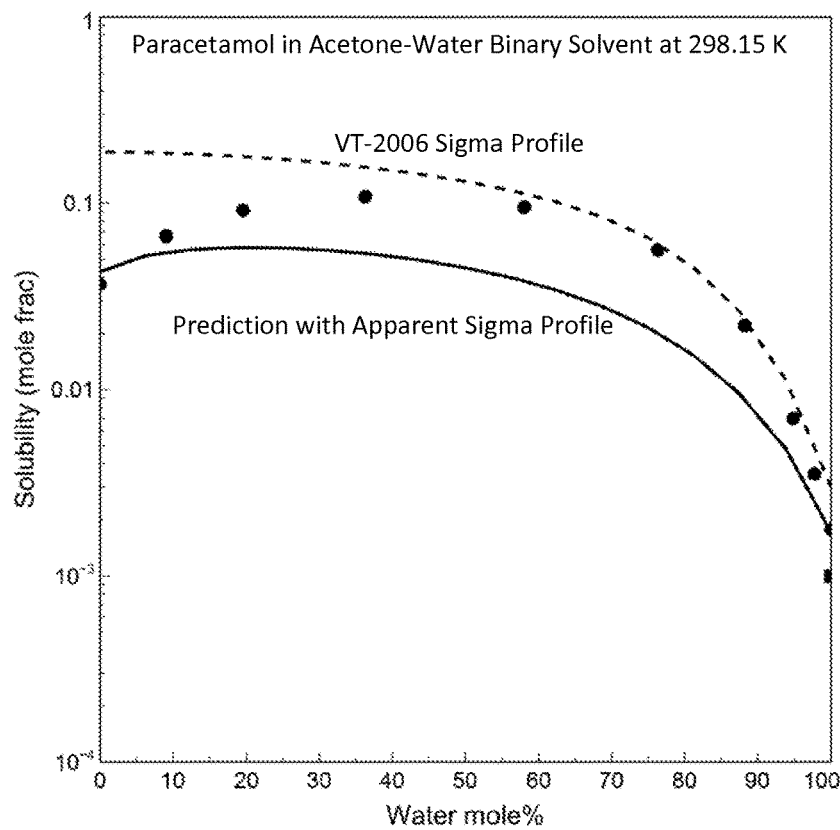
FIG. 10 is a graph showing the model predictions and the experimental data of paracetamol solubility in acetone-water binary at 298.15 K in accordance with one embodiment of the present invention.

FIG. 10 shows the model predictions and the experimental data of paracetamol solubility in acetone-water binary at 298.15 K: experimental data (•), experimental data (■), prediction with VT-2006 sigma profile (dashed line), and prediction with apparent sigma profile (solid line). The VT-2006 sigma profile over predicts the solubility at low water content and yields reasonable solubility results when the water content exceeds 50 mol %. However, the VT-2006 sigma profile fails to predict a solubility maximum that is clearly shown by the experimental data. On the other hand, the predictions from the apparent sigma profile show a maximal solubility in the binary system that seems to be consistent with the experimental solubility trend.

Figure 11:
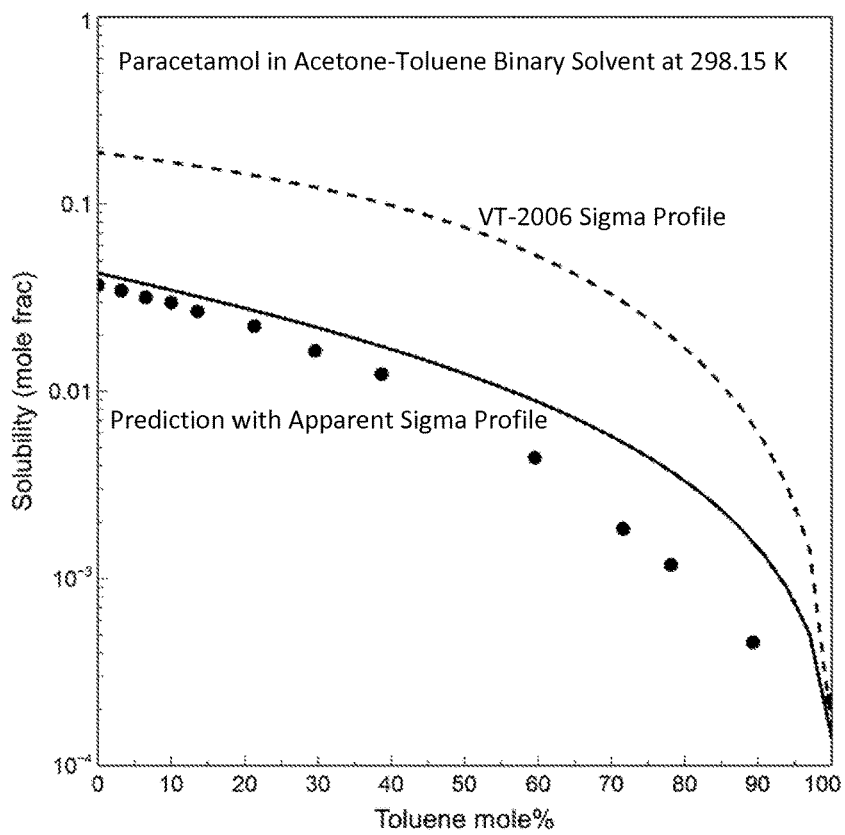
FIG. 11 is a graph showing the model predictions and the experimental data of paracetamol solubility in acetone-toluene binary at 298.15 K in accordance with one embodiment of the present invention.

FIG. 11 shows the model predictions and the experimental data of paracetamol solubility in acetone-toluene binary at 298.15 K: experimental data (•), prediction with VT-2006 sigma profile (dashed line), and prediction with apparent sigma profile (solid line). Both the apparent sigma profile predictions and the VT-2006 predictions show similar trends. The VT-2006 sigma profile overpredicts the paracetamol solubility throughout the entire concentration range except for pure toluene. The apparent sigma profile predictions are much closer to the data.

Figure 12:
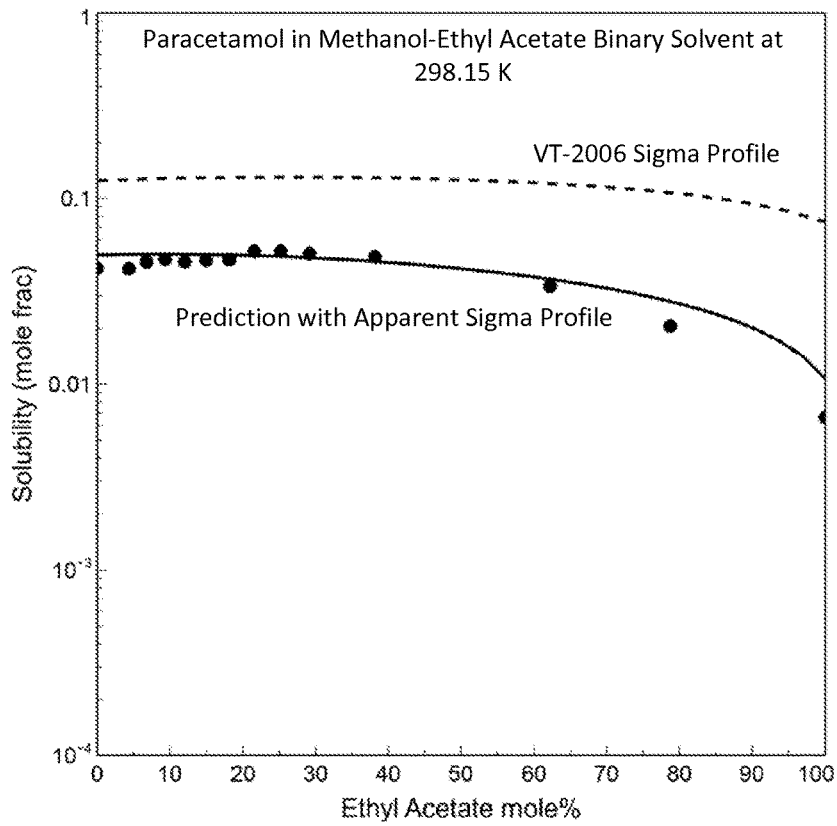
FIG. 12 is a graph showing the model predictions and experimental data of paracetamol solubility in methanol-ethyl acetate binary at 298.15 K in accordance with one embodiment of the present invention.

FIG. 12 shows the model predictions and experimental data of paracetamol solubility in methanol-ethyl acetate binary at 298.15 K: experimental data (•), prediction with VT-2006 sigma profile (dashed line), and prediction with apparent sigma profile (solid line). Both the apparent sigma profile predictions and the VT-2006 predictions show similar trends. The VT-2006 sigma profile overpredicts the paracetamol solubility for the entire binary system, whereas the apparent sigma profile predictions follow the experimental data well.

LOVASTATIN: For lovastatin, the melting temperature and enthalpy of fusion are reported as 444.25 K and 36530 kJ/kmol, respectively. From these thermodynamic properties the logarithm of solubility constant, i.e., $\ln K_{sp}$, is calculated to be −4.83 at 298.15 K.

Figure 13:
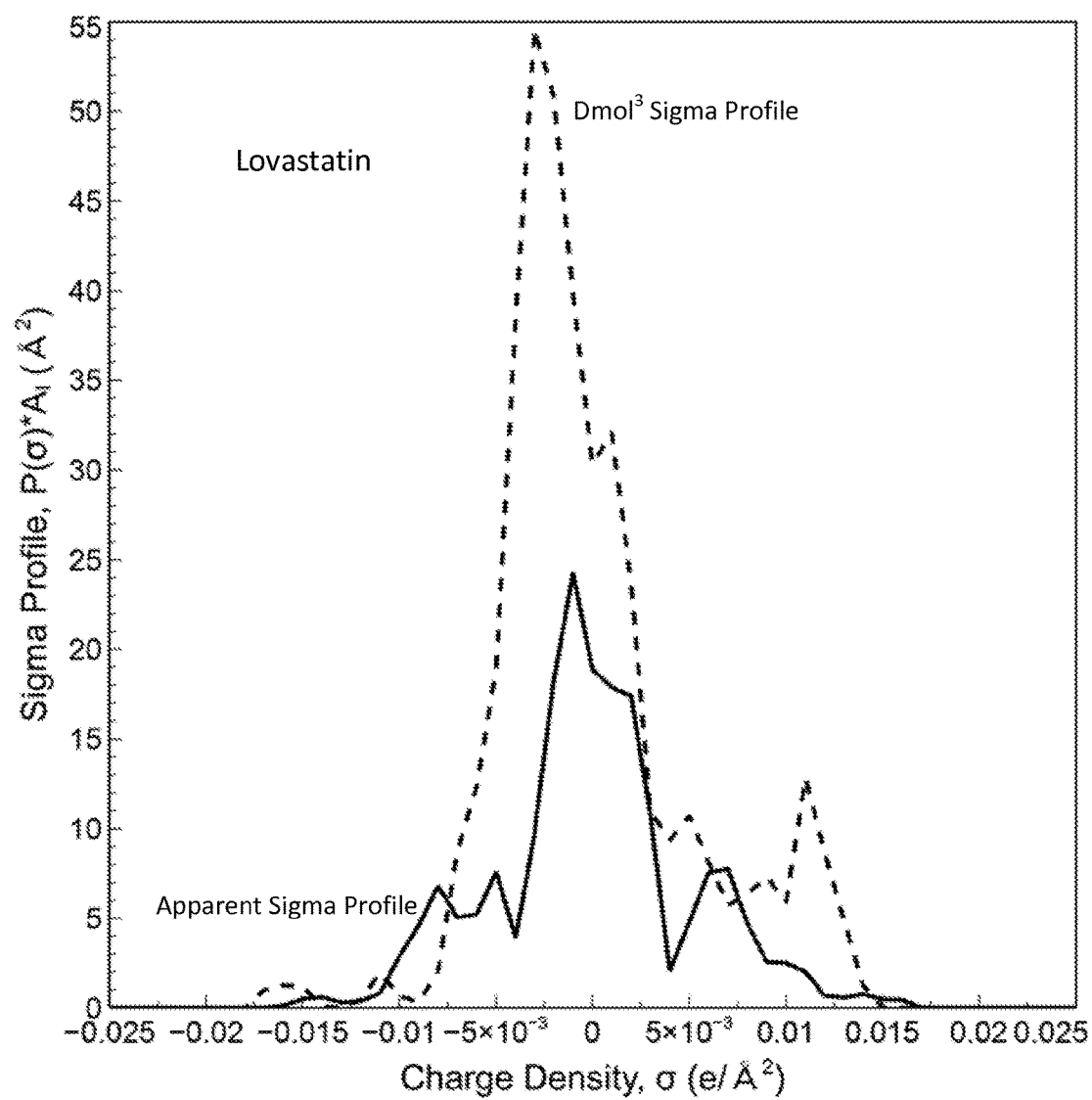
FIG. 13 is a graph showing the apparent sigma profile of lovastatin together with the DMol$^3$ sigma profile in accordance with one embodiment of the present invention.

Unlike the other three drug molecules, the sigma profile of lovastatin is not included in VT-2006 database. Therefore, the sigma profile of lovastatin is computed using $DMol^3$ module of Accelrys Materials Studio software package. The procedure for sigma profile generation outlined in the literature was followed. The computed sigma profile is shown in FIG. 13. The most noticeable feature of the $DMol^3$-generated sigma profile for lovastatin is its very high level of hydrophobic segments.

The available experimental solubility data for lovastatin in 18 pure solvents are reported in Table 10. To identify the conceptual segment numbers for lovastatin, the solubility data of four solvents, i.e., ethyl acetate, acetone, methanol, and 1-octanol, was regressed. The regressed conceptual segment numbers are reported in Table 11. The apparent sigma profile (solid line) for lovastatin is shown in FIG. 13 along with the one generated from $DMol^3$ (dashed line). The estimated conceptual segment numbers indicate relatively high hydrophobic segments and polar attractive segments. The conceptual segment numbers remain similar even when all the solubility data for the 18 solvents are used (Table 11). The apparent sigma profile shows significant hydrophobic segments but much lower than that of the $DMol^3$-generated sigma profile. The apparent cavity volume is calculated to be 251.45 $Å^3$. In comparison, the $DMol^3$ module reported the cavity volume of lovastatin molecule as 521.55 $Å^3$.

TABLE 10

Experimental and Calculated Solubility of Lovastatin

| Solvent | Temp (K) | Experimental Solubility (mole frac) | Calculated Solubility DMol³ Sigma Profile (mole frac) | Calculated Solubility Apparent Sigma Profile (mole frac) |
|---|---|---|---|---|
| ethyl-acetate[a] | 297.20 | $6.56 \times 10^{-3}$ | $8.17 \times 10^{-3}$ | $6.56 \times 10^{-3}$ |
| acetone[a] | 297.20 | $1.30 \times 10^{-2}$ | $2.88 \times 10^{-2}$ | $1.30 \times 10^{-2}$ |
| methanol[a] | 298.35 | $3.15 \times 10^{-3}$ | $8.07 \times 10^{-3}$ | $3.15 \times 10^{-3}$ |
| 1-octanol[a] | 301.20 | $4.67 \times 10^{-3}$ | $4.17 \times 10^{-3}$ | $4.67 \times 10^{-3}$ |
| methyl acetate | 297.20 | $4.47 \times 10^{-3}$ | $9.97 \times 10^{-3}$ | $6.63 \times 10^{-3}$ |
| N-propyl acetate | 297.20 | $5.87 \times 10^{-3}$ | $6.42 \times 10^{-3}$ | $6.11 \times 10^{-3}$ |
| iso-propyl acetate | 297.20 | $4.97 \times 10^{-3}$ | $8.99 \times 10^{-3}$ | $7.10 \times 10^{-3}$ |
| N-butyl acetate | 297.20 | $6.11 \times 10^{-3}$ | $5.03 \times 10^{-3}$ | $5.62 \times 10^{-3}$ |
| isobutyl acetate | 297.20 | $5.04 \times 10^{-3}$ | $6.77 \times 10^{-3}$ | $6.44 \times 10^{-3}$ |
| sec-butyl acetate | 297.20 | $5.45 \times 10^{-3}$ | $7.55 \times 10^{-3}$ | $6.88 \times 10^{-3}$ |
| tert-butyl acetate | 297.20 | $4.20 \times 10^{-3}$ | $1.01 \times 10^{-2}$ | $7.28 \times 10^{-3}$ |
| 2-butanone | 297.20 | $1.15 \times 10^{-2}$ | $2.87 \times 10^{-2}$ | $1.34 \times 10^{-2}$ |
| ethanol | 298.15 | $3.53 \times 10^{-3}$ | $1.10 \times 10^{-2}$ | $4.76 \times 10^{-3}$ |
| 1-propanol | 301.65 | $6.50 \times 10^{-3}$ | $1.04 \times 10^{-2}$ | $5.58 \times 10^{-3}$ |
| N-butanol | 301.20 | $7.02 \times 10^{-3}$ | $8.44 \times 10^{-3}$ | $5.37 \times 10^{-3}$ |
| 1-pentanol | 299.20 | $4.68 \times 10^{-3}$ | $5.96 \times 10^{-3}$ | $4.64 \times 10^{-3}$ |
| 1-hexanol | 298.95 | $4.04 \times 10^{-3}$ | $5.07 \times 10^{-3}$ | $4.47 \times 10^{-3}$ |
| water | 298.15 | $1.78 \times 10^{-8}$ | $2.34 \times 10^{-7}$ | $4.70 \times 10^{-6}$ |

[a]Solvents used for conceptual segment number estimation

TABLE 11

Conceptual Segment Numbers for Lovastatin

| Conceptual Segment | Segment Numbers | |
|---|---|---|
| | 4 Solvents | All Solvents |
| X | 0.670 | 1.044 |
| Y$^-$ | 0.038 | 0 |
| Y$^+$ | 0.840 | 0.665 |
| Z | 0.202 | 0.212 |

Figure 14:
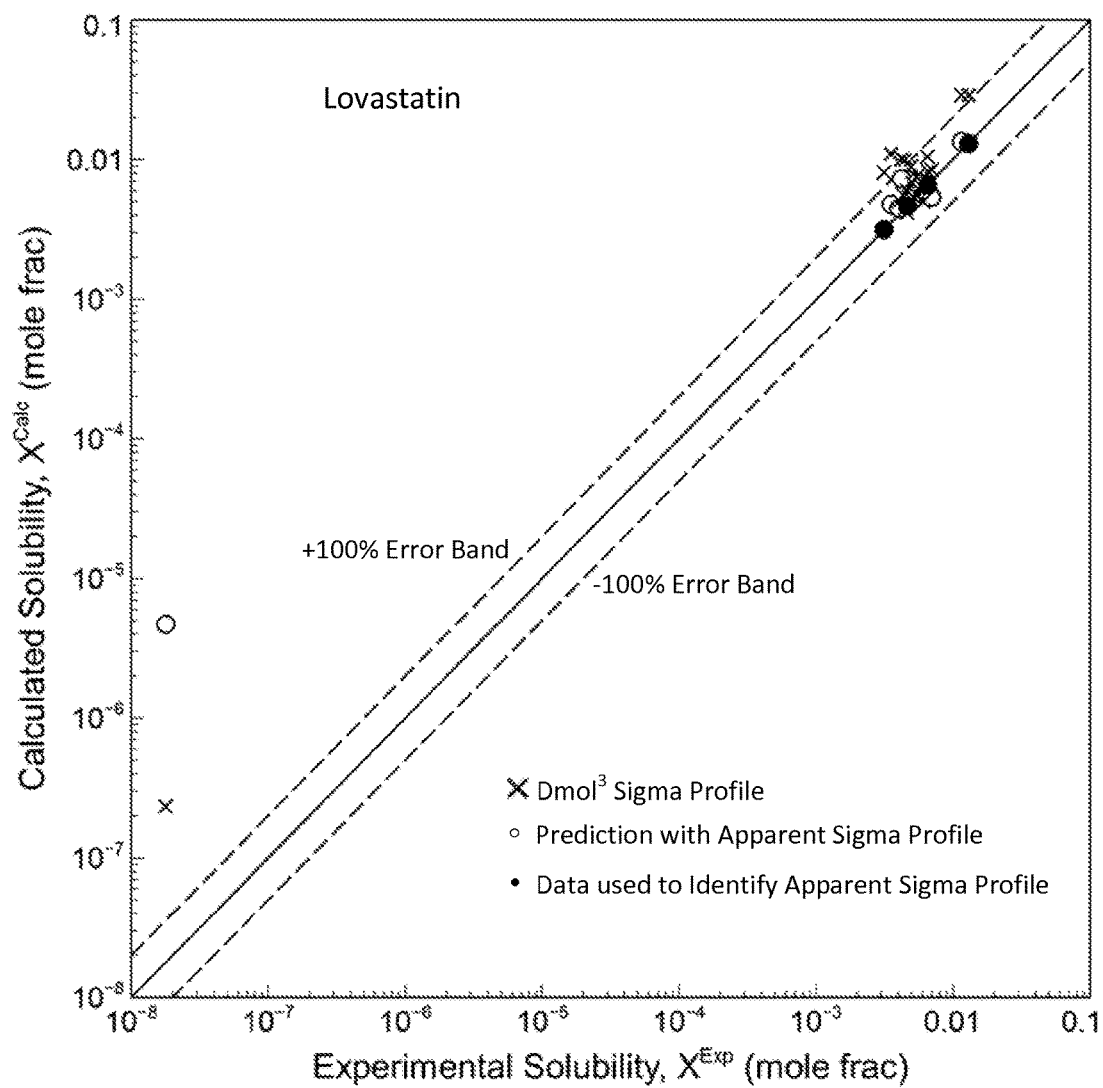
FIG. 14 is a graph showing the parity plot comparing the experimental and calculated solubilities for lovastatin in accordance with one embodiment of the present invention.

Solubility of lovastatin in the 18 pure solvents is calculated using both the apparent sigma profile and the DMol$^3$-generated sigma profile. The calculated results are presented in Table 10 together with their experimental values. A parity plot is included in FIG. 14 to demonstrate the effectiveness of these two sigma profiles: prediction with DMol$^3$ sigma profile (×), prediction with apparent sigma profile (○), data used to identify apparent sigma profile (•), ±100% error band (dashed lines). The DMol$^3$-generated sigma profile slightly over predicts the lovastatin solubility in all solvents except for 1-octanol and n-butyl acetate. The apparent sigma profile predicts solubility in all solvents well except for water. The model errors for lovastatin solubility calculation are reported in Table 12 for both the apparent sigma profile and the DMol$^3$-generated sigma profile. The RMSE for the apparent sigma profile estimated from four solvents assumes the highest value. This is due to the poor prediction of lovastatin solubility in water. Lovastatin is sparingly soluble in water, and its solubility is difficult to ascertain. If the water solubility prediction is excluded from the RMSE calculation, the RMSE for the apparent sigma profile drops drastically from 1.33 to 0.23.

TABLE 12

RMSE in Logarithm of Solubility of Lovastatin in 18 Pure Solvents

| DMol$^3$ | Apparent Sigma Profile | |
|---|---|---|
| Sigma Profile | 4 Solvents | All Solvents |
| 0.84 | 1.33 | 0.70 |
| 0.60$^a$ | 0.23$^a$ | 0.54$^a$ |

$^a$With water excluded

Figure 15:
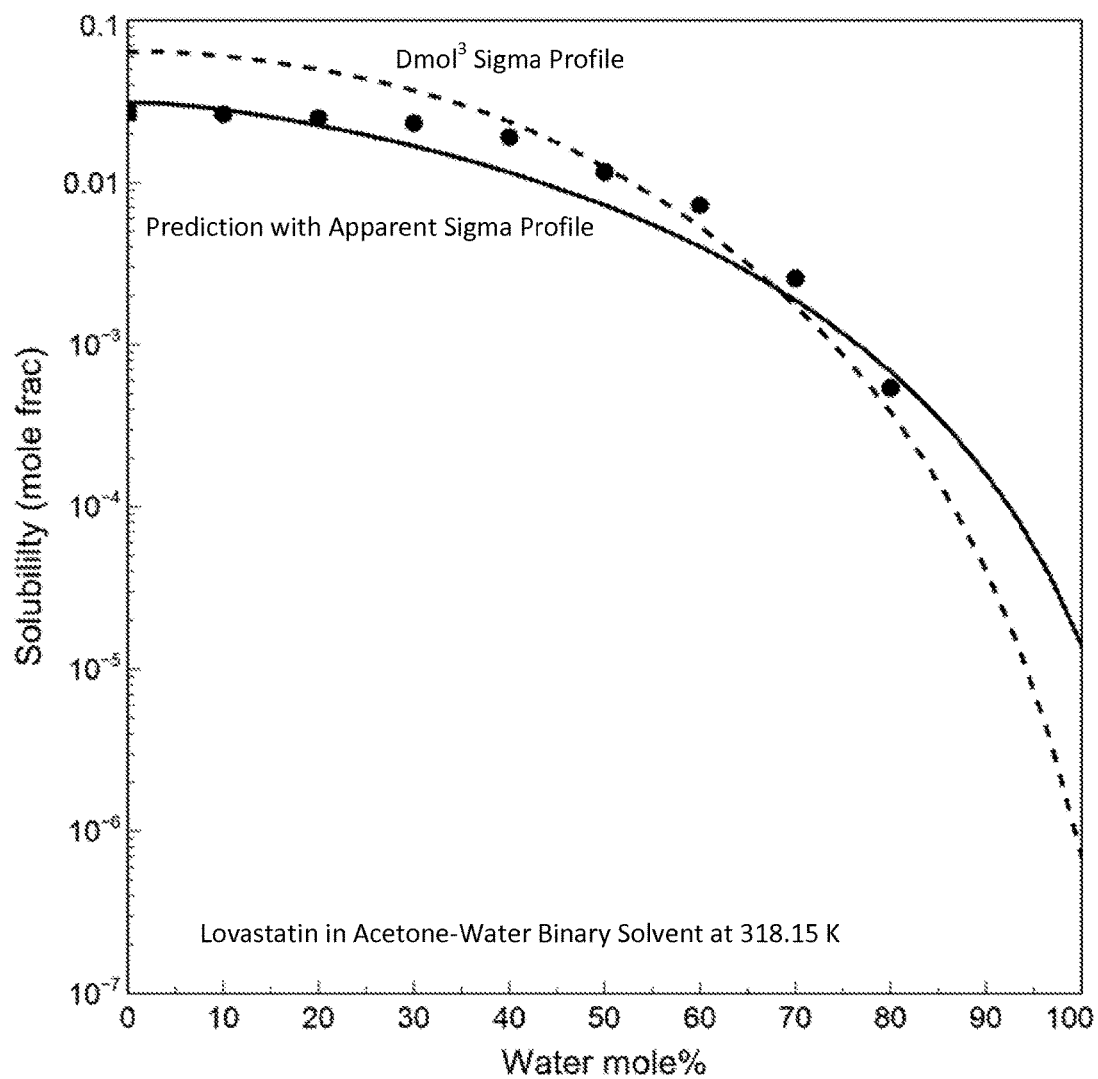
FIG. 15 is a graph showing the prediction results for lovastatin solubility in acetone-water binary with the apparent sigma profile and the DMol$^3$-generated sigma profile in accordance with one embodiment of the present invention.

The lovastatin solubility is further predicted in acetone-water binary solvent. The experimental solubility data in the binary solvent at 318.15 K are available along with the lovastatin solubility in pure acetone. However, no experimental solubility of lovastatin in water at 318.15 K was found. FIG. 15 shows the prediction results for lovastatin solubility in acetone-water binary with the apparent sigma profile (solid line) and the DMol$^3$-generated sigma profile (dashed line), experimental data (■), and experimental data (•). The prediction results from both sigma profiles show a similar solubility trend against water content. The apparent sigma profile predicts lovastatin solubility in acetone very close to their experimental value, whereas the DMol$^3$-generated sigma profile slightly over predicts lovastatin solubility in the acetone-rich region.

Figure 16:
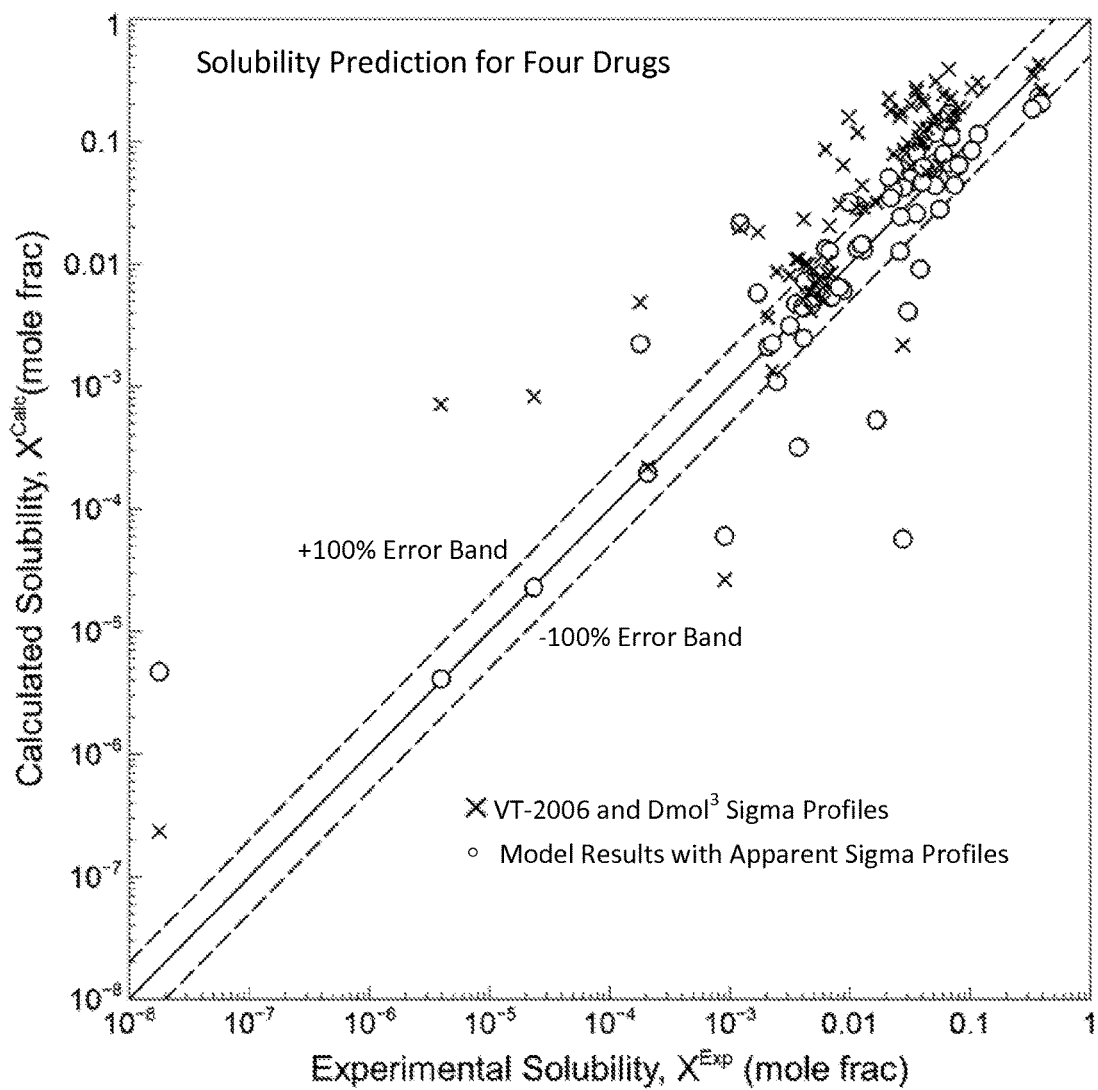
FIG. 16 is a graph showing the parity plot for all the pure solvent solubility data and model results for the four drug molecules in accordance with one embodiment of the present invention.

To summarize the results for the four drug molecules, FIG. 16 shows the parity plot for all the pure solvent solubility data and model results for the four drug molecules: prediction with VT-2006 and DMol$^3$ sigma profiles (×), model results with apparent sigma profiles (○), ±100% error band (dashed line). With the 75 solubility data investigated, 29% of the predicted solubilities fall inside the ±100% error band when the sigma profiles from VT-2006 and DMol$^3$ are used. Most of the predicted solubilities are higher than the experimental values. On the other hand, 73% of the solubilities calculated with the apparent sigma profiles fall inside the ±100% error band. It should be emphasized that the model results with VT-2006 and DMol$^3$ sigma profiles represent COSMO-SAC predictions without the use of the experimental data.

The conceptual segment numbers of NRTL-SAC model for the four drug molecules, published in the literature, are reported in Table 13. It is interesting that the conceptual segment numbers determined in this study for COSMO-SAC apparent sigma profiles are largely in line with their NRTL-SAC counterparts. The dominant conceptual segments identified by NRTL-SAC for the four drug molecules are also identified by the apparent sigma profiles. Obviously, the two sets of conceptual segment numbers are not exactly the same because different sets of reference molecules are selected for the two models.

TABLE 13

NRTL-SAC Conceptual Segment Numbers for Four Drug Molecules

| Conceptual Segment | Segment Numbers | | | |
|---|---|---|---|---|
| | Caffeine | Aspirin | Paracetamol | Lovastatin |
| X | −0.105 | 0.103 | 0.498 | 0.175 |
| Y$^-$ | 0.282 | 0 | 0.487 | 0 |
| Y$^+$ | 1.211 | 1.160 | 0.162 | 0.548 |
| Z | 0.211 | 0.777 | 1.270 | 0.882 |

The present invention offers a simple and practical approach for generating empirical, apparent sigma profile of any molecule from available experimental solubility data or other relevant phase equilibrium data. The present invention requires no knowledge of molecular structure, no use of DFT calculations, and no quantum chemistry packages. Incorporating the conceptual segment concept, the present invention generates apparent sigma profiles from sigma profiles for conceptual segment reference molecules, and the necessary conceptual segment numbers are identified from fitting against experimental solubility data. The present invention allows use of valuable experimental measurements as input to the COSMO-based models and transforms COSMO-SAC into a correlative model. The apparent sigma profiles represent "best-fit" profiles against experimental data and can be used for further predictions. The sigma profile generation methodology should enhance the usability of the COSMO-based thermodynamic models in the predictions of liquid-phase nonideality and fluid-phase equilibria.

Figure 17:
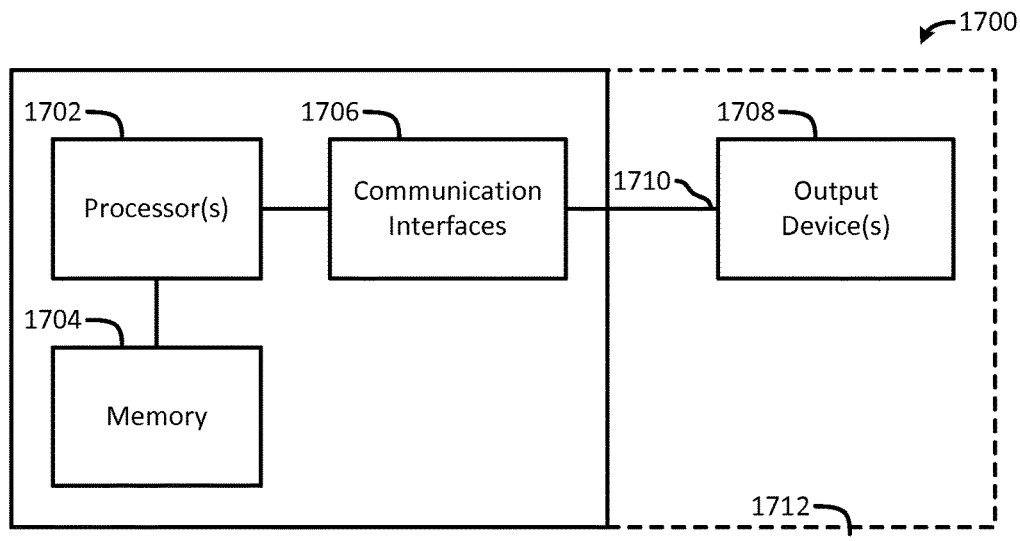
FIG. 17 is a block diagram of an apparatus suitable for performing the methods of FIGS. 2 and 18-20.

Some other embodiments of the present invention will now be described with respect to FIGS. 17-20. FIG. 17 is a block diagram of a computer 1700, such as a workstation, laptop, desktop, tablet computer, mainframe, or other single or distributed computing platform suitable for performing the methods described herein. Note that the components can be integrated into a single device or communicably coupled to one another via a network. The computer 1700 includes one or more processors 1702, a memory 1704, and one or more communication interfaces 1706, which can be communicably coupled to one or more output device(s) 1708 (e.g., printer, internal or external data storage device, display or monitor, remote database, remote computer, etc.) via a network or communications link 1710 (e.g., wired, wireless, optical, etc.). The one or more output device(s) can be integrated into the computer 1700 as indicated by the dashed line 1712.

Figure 18:
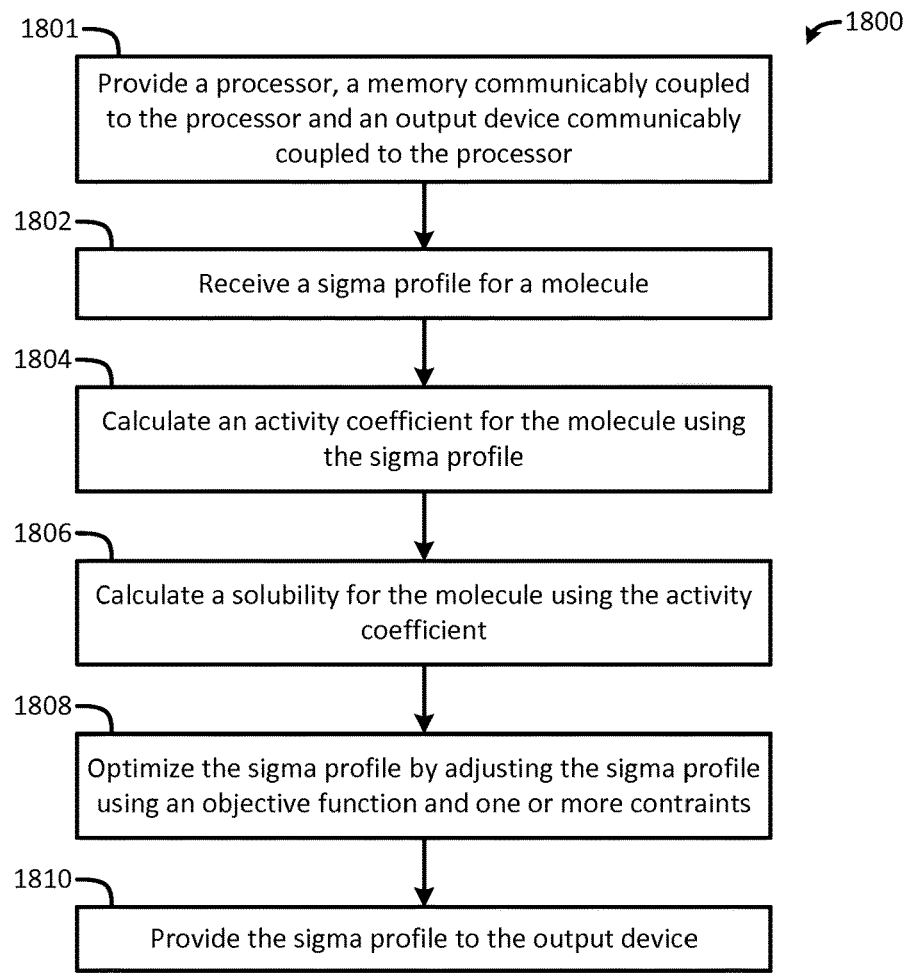
FIG. 18 is a flow chart of a method for optimizing sigma profiles in accordance with another embodiment of the present invention.

Now referring to FIG. 18, a computerized method 1800 for optimizing a sigma profile for a molecule in accordance with another embodiment of the present invention is shown. A processor, a memory communicably coupled to the processor and an output device communicably coupled to the processor is provided in block 1801. A sigma profile for the molecule is received in block 1802. An activity coefficient for the molecule is calculated in block 1804 using the sigma profile for the molecule using a processor. A solubility for the molecule is calculated in block 1806 using the activity coefficient for the molecule using the processor. The sigma profile for the molecule is optimized in block 1808 by adjusting the sigma profile using an objective function and one or more constraints using the processor. The sigma profile is provided to the output device in block 1810. The sigma profile can then be used in a conductor like screening model. Note that the sigma profile can be optimized without any identification of a molecular structure of the molecule, or without using any quantum mechanics calculations. The method 1800 can be implemented by the apparatus 1700 or by a non-transitory computer readable medium encoded with a computer program for execution by a processor that performs the steps of the method 1800.

The method 1800 may also include the steps of determining whether the sigma profile has converged using the objective function and the one or more constraints using the computer, and whenever the sigma profile has not converged, repeating the activity coefficient calculation step, the solubility calculation step, the sigma profile adjustment step and the determination step using the computer. The sigma profile can converge when a change in the sigma profile is less than equal to a threshold value, the change in the sigma profile increases, a maximum number of iterations have been completed, or other desired metric.

The sigma profile for the molecule can be received in block 1802 by: (1) obtaining the sigma profile from a database; (2) generating the sigma profile for the molecule using a set of sigma profile vectors for a reference hydrophobicity solvent, a reference solvation solvent, a reference polarity solvent and a reference hydrophilicity solvent; (3) generating the sigma profile for the molecule using a vapor-liquid equilibrium data for a reference hydrophobicity solvent, a reference solvation solvent, a reference polarity solvent and a reference hydrophilicity solvent; or (4) other desired method. This may include the steps of selecting the reference hydrophobicity solvent, the reference solvation solvent, the reference polarity solvent and the reference hydrophilicity solvent, and obtaining the set of sigma profile vectors of the reference hydrophobicity solvent, the reference solvation solvent, the reference polarity solvent and the reference hydrophilicity solvent.

Figure 19:
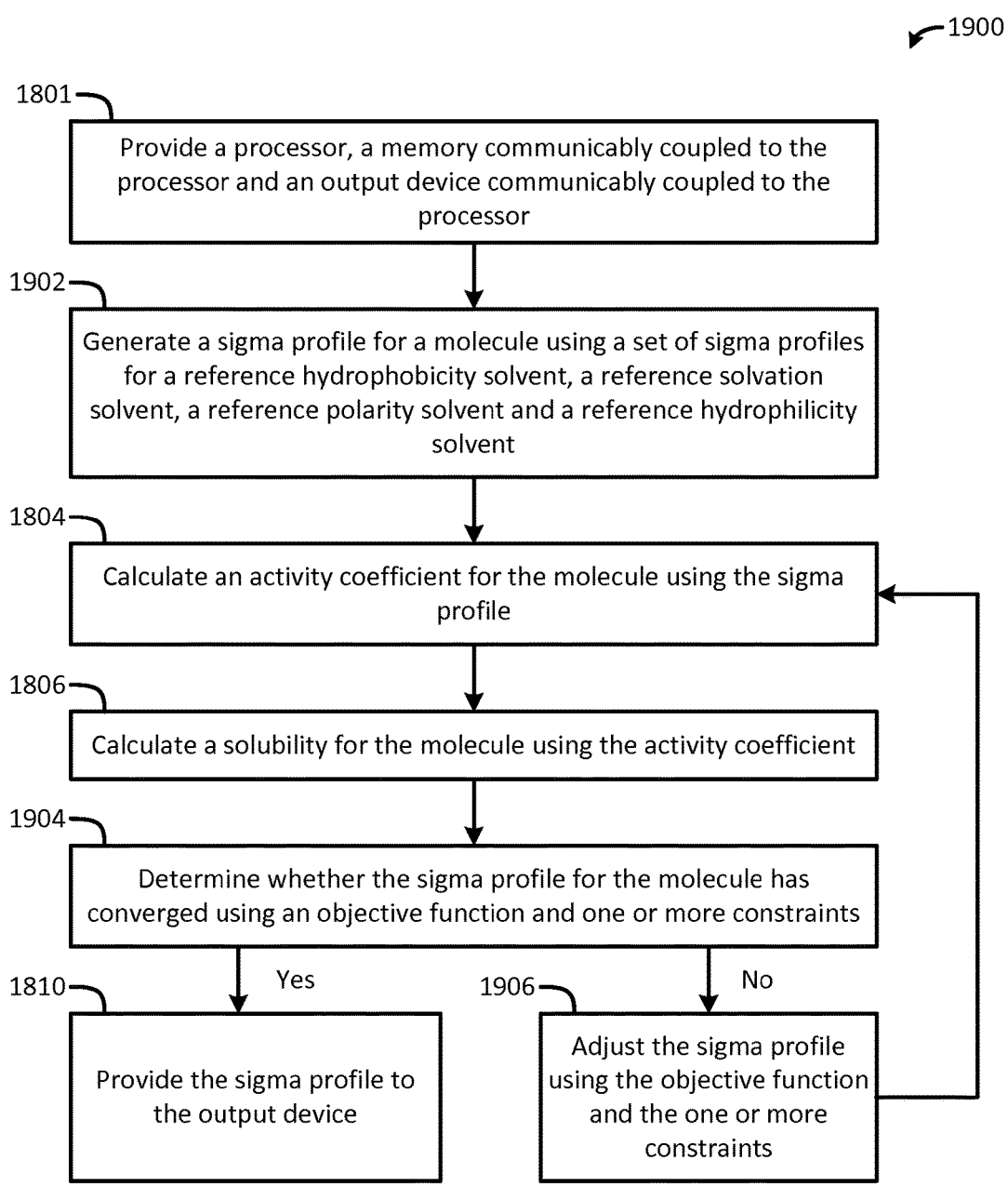
FIG. 19 is a flow chart of a method for generating sigma profiles in accordance with another embodiment of the present invention.

Referring now to FIG. 19, a computerized method 1900 for generating a sigma profile for a molecule in accordance with another embodiment of the present invention is shown. A processor, a memory communicably coupled to the processor and an output device communicably coupled to the processor is provided in block 1801. A sigma profile for the molecule is generated in block 1902 using a set of sigma profile vectors for a reference hydrophobicity solvent, a reference solvation solvent, a reference polarity solvent and a reference hydrophilicity solvent.

An activity coefficient for the molecule is calculated in block 1804 using the sigma profile for the molecule using a computer. A solubility for the molecule is calculated in block 1806 using the activity coefficient for the molecule using a computer. A determination of whether the sigma profile has converged is made in block 1904 using an objective function and one or more constraints using the computer (e.g., a change in the sigma profile is less than equal to a threshold value, the change in the sigma profile increases, or a maximum number of iterations have been completed, etc.). If the sigma profile has not converged, as determined in block 1904, the sigma profile for the molecule is adjusted using the objective function and the one or more constraints in block 1906 and the process repeats by looping back to block 1804. If, however, the sigma profile has converged, as determined in block 1904, the sigma profile is provided to the output device in block 1810. The sigma profile can then be used in a conductor like screening model. Note that the sigma profile can be optimized without any identification of a molecular structure of the molecule, or without using any quantum mechanics calculations. The method 1900 can be implemented by the apparatus 1700 or by a non-transitory computer readable medium encoded with a computer program for execution by a processor that performs the steps of the method 1900.

In FIGS. 18-19, the sigma profile for the molecule (blocks 1802, 1902) can be generated using a coefficient vector defined by:

$$p_I(\sigma)A_I = A_{ref}\begin{bmatrix} X \\ Y^- \\ Y^+ \\ Z \end{bmatrix}$$

where $A_{ref}$ is a matrix generated from the sigma profile vector of the reference hydrophobicity solvent, the reference solvation solvent, the reference polarity solvent and the reference hydrophilicity solvent, and $[X, Y^-, Y^+, Z]^T$ is a coefficient vector of hydrophobicity (X), solvation ($Y^-$), polarity ($Y^+$) and hydrophilicity (Z) at a specific temperature T.

In FIGS. 18-19, the calculation of the activity coefficient for the molecule (block 1804) can be represented by:

$$\ln\gamma_{I/S} = n_I \sum_{\sigma_m} p_I(\sigma_m)[\ln\Gamma_S(\sigma_m) - \ln\Gamma_I(\sigma_m)] + \ln\gamma_{I/S}^{SG}$$

where $\ln \gamma_{I/S}$ is a natural logarithm of the activity coefficient for the molecule, $\sigma_m$ is a charge density of a segment m, $p_I(\sigma_m)$ is the generated sigma profile for the molecule, $\ln \Gamma_I(\sigma^m)$ is a natural logarithm of a segment activity coefficient for the molecule, $\ln \Gamma_S(\sigma^m)$ is a natural logarithm of a segment activity coefficient for a mixture of the molecule and a solvent, and $\ln \gamma_{I/S}^{SG}$ is a natural logarithm of a Staverman-Guggenheim activity coefficient.

Figure 20:
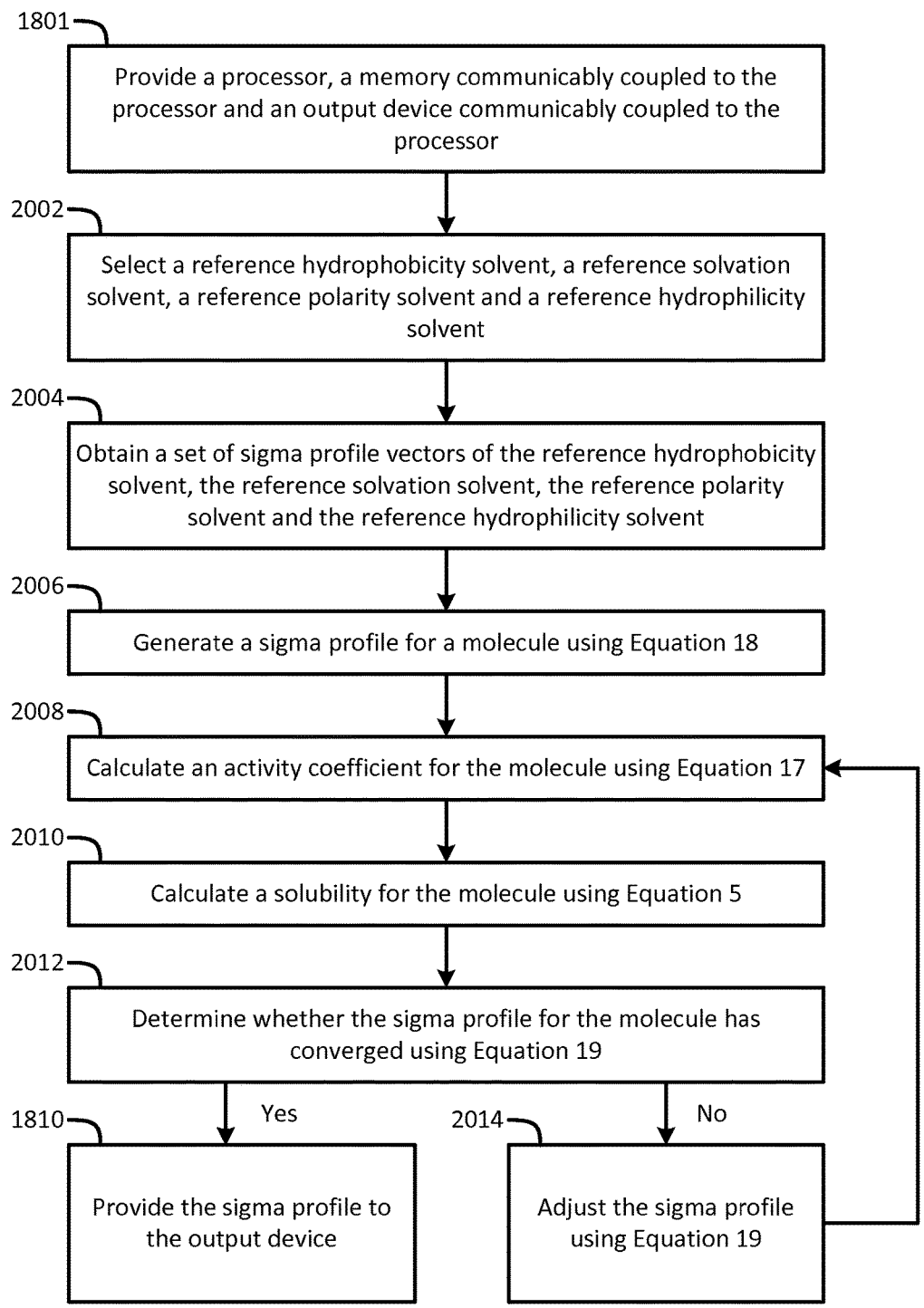
FIG. 20 is a flow chart of a method for generating sigma profiles in accordance with another embodiment of the present invention.

In FIGS. 18-20, the calculation of the solubility of the molecule (blocks 1806 and 2010) can be represented by:

$$\ln x_I^{sat}\gamma_I^{sat} = \frac{\Delta H_{fus}}{R}\left(\frac{1}{T_m} - \frac{1}{T}\right)$$

where $\ln x_I^{sat}\gamma_I^{sat}$ is a natural logarithm of the solubility and calculated activity coefficient of the molecule, $\Delta H_{fus}$ is a enthalpy of fusion, R is a universal gas constant, $T_m$ is a melting temperature, and T is a specific temperature.

The calculation of the solubility of the molecule (block 1806) can also be represented by:

$$\ln x_I^{sat} \gamma_I^{sat} = \ln K_{sp}$$

where $\ln x_I^{sat} \gamma_I^{sat}$ is a natural logarithm of the solubility and calculated activity coefficient of the molecule, and $\ln K_{sp}$ is a natural logarithm of an adjustable parameter regressed from an experimental solubility data for the molecule.

The calculation of the solubility of the molecule (block 1806) may also include the step of calculating the adjustable parameter from the experimental solubility data for the molecule using a regression analysis.

In FIGS. 18-19, the objective function and the one or more constraints (blocks 1808, 1904, 1906) minimize an error between the calculated solubility for the molecule and an experimental solubility for the molecule. The objective function and the one or more constraints can be represented by:

$$\underset{XY^-Y^+Z}{\text{minimize}} \frac{1}{n} \sum_j^n [\ln x_j^{exp} - \ln x_j^{calc}]^2$$

subject to $$p_I(\sigma) \geq 0$$

where $x_j^{exp}$ is a experimental solubility of the molecule, $\ln x_j^{calc}$ is the calculated solubility of the molecule, and $p_I(\sigma)$ is the generated sigma profile for the molecule.

Now referring to FIG. 20, a computerized method 2000 for generating a sigma profile for a molecule in accordance with another embodiment of the present invention is shown. A processor, a memory communicably coupled to the processor and an output device communicably coupled to the processor is provided in block 1801. A reference hydrophobicity solvent, a reference solvation solvent, a reference polarity solvent and a reference hydrophilicity solvent are selected in block 2002. A set of sigma profile vectors of the reference hydrophobicity solvent, the reference solvation solvent, the reference polarity solvent and the reference hydrophilicity solvent are obtained in block 2004. The sigma profile for the molecule is generated in block 2006 using a coefficient vector defined by:

$$p_I(\sigma)A_I = A_{ref} \begin{bmatrix} X \\ Y^- \\ Y^+ \\ Z \end{bmatrix}$$

where $A_{ref}$ is a matrix generated from the sigma profile vector of the reference hydrophobicity solvent, the reference solvation solvent, the reference polarity solvent and the reference hydrophilicity solvent, and $[X, Y^-, Y^+, Z]^T$ is a coefficient vector of hydrophobicity (X), solvation ($Y^-$), polarity ($Y^+$) and hydrophilicity (Z) at a specific temperature T. An activity coefficient for the molecule is calculated in block 2008 using the sigma profile for the molecule using a computer wherein the activity coefficient is represented by:

$$\ln \gamma_{I/S} = n_I \sum_{\sigma_m} p_I(\sigma_m)[\ln \Gamma_S(\sigma_m) - \ln \Gamma_I(\sigma_m)] + \ln \gamma_{I/S}^{SG}$$

where $\ln \gamma_{I/S}$ is a natural logarithm of the activity coefficient for the molecule, $\sigma_m$ is a charge density of a segment m, $p_I(\sigma_m)$ is the generated sigma profile for the molecule, $\ln \Gamma_I(\sigma_m)$ is a natural logarithm of a segment activity coefficient for the molecule, $\ln \Gamma_S(\sigma_m)$ is a natural logarithm of a segment activity coefficient for a mixture of the molecule and a solvent, and $\ln \gamma_{I/S}^{SG}$ is a natural logarithm of a Staverman-Guggenheim activity coefficient.

A solubility for the molecule is calculated in block 2010 using the activity coefficient for the molecule using the computer. A determination of whether the sigma profile has converged is made in block 2012 using an objective function and one or more constraints using the computer (e.g., a change in the sigma profile is less than equal to a threshold value, the change in the sigma profile increases, or a maximum number of iterations have been completed, etc.), wherein objective function and the one or more constraints can be represented by:

$$\underset{XY^-Y^+Z}{\text{minimize}} \frac{1}{n} \sum_j^n [\ln x_j^{exp} - \ln x_j^{calc}]^2$$

subject to $$p_I(\sigma) \geq 0$$

where $x_j^{exp}$ is a experimental solubility of the molecule, $\ln x_j^{calc}$ is the calculated solubility of the molecule, and $p_I(\sigma)$ is the generated sigma profile for the molecule.

If the sigma profile has not converged, as determined in block 2012, the sigma profile for the molecule is adjusted using the objective function and the one or more constraints in block 2014 and the process repeats by looping back to block 2008. If, however, the sigma profile has converged, as determined in block 2012, the sigma profile is provided to the output device in block 1810. The sigma profile can then be used in a conductor like screening model. Note that the sigma profile can be optimized without any identification of a molecular structure of the molecule, or without using any quantum mechanics calculations. The method 2000 can be implemented by the apparatus 1700 or by a non-transitory computer readable medium encoded with a computer program for execution by a processor that performs the steps of the method 2000.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the systems, devices, computer programs, compositions and/or methods disclosed and claimed herein can be made and executed without undue experimentation in light of the present disclosure. While the systems, devices, computer programs, compositions and methods of this invention have been described in terms of preferred embodiments, it will be apparent to those of skill in the art that variations may be applied to the systems, devices, computer programs, compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The invention claimed is:

1. A computerized method for optimizing a sigma profile for a molecule comprising the steps of:
    providing a processor, a memory communicably coupled to the processor and an output device communicably coupled to the processor;
    receiving the sigma profile for the molecule;
    calculating an activity coefficient for the molecule using the sigma profile for the molecule using the processor;
    calculating a solubility for the molecule using the activity coefficient for the molecule using the processor;
    optimizing the sigma profile for the molecule by adjusting the sigma profile using an objective function and one or more constraints to minimize an error between the calculated solubility for the molecule and an experimental solubility for the molecule using the processor, wherein the objective function and the one or more constraints are represented by:

$$\underset{XY^-Y^+Z}{minimize} \frac{1}{n} \sum_{j}^{n} [\ln x_j^{exp} - \ln x_j^{calc}]^2$$

subject to $$p_I(\sigma) \geq 0$$

where X, Y$^-$, Y$^+$, Z is a coefficient vector of hydrophobicity (X), solvation (Y$^-$), polarity (Y$^+$) and hydrophilicity (Z), n is number of data points, $x_j^{exp}$ is the experimental solubility of the molecule, ln $x_j^{calc}$ is calculated solubility of the molecule, $p_I(\sigma)$ is the generated sigma profile for the molecule;
    providing the optimized sigma profile to the output device; and
    developing a chemical process or product using the optimized sigma profile.

2. The method as recited in claim 1, further comprising the steps of:
    determining whether the sigma profile has converged using the objective function and the one or more constraints using the processor; and
    whenever the sigma profile has not converged, repeating the activity coefficient calculation step, the solubility calculation step, the sigma profile adjustment step and the determination step using the processor.

3. The method as recited in claim 2, wherein the sigma profile converges when a change in the sigma profile is less than or equal to a threshold value, the change in the sigma profile increases, or a maximum number of iterations have been completed.

4. The method as recited in claim 1, wherein the step of receiving the sigma profile for the molecule comprises generating the sigma profile for the molecule using a set of sigma profile vectors for a reference hydrophobicity solvent, a reference solvation solvent, a reference polarity solvent and a reference hydrophilicity solvent.

5. The method as recited in claim 4, wherein the sigma profile is optimized without any identification of a molecular structure of the molecule.

6. The method as recited in claim 4, wherein the sigma profile is optimized without using any density functional theory (DFT) calculations or quantum mechanics calculations.

7. The method as recited in claim 4, further comprising the steps of:
    selecting the reference hydrophobicity solvent, the reference solvation solvent, the reference polarity solvent and the reference hydrophilicity solvent; and
    obtaining the set of sigma profile vectors of the reference hydrophobicity solvent, the reference solvation solvent, the reference polarity solvent and the reference hydrophilicity solvent.

8. The method as recited in claim 7, wherein the reference hydrophobicity solvent, the reference solvation solvent, the reference polarity solvent and the reference hydrophilicity solvent are selected from the group consisting essentially acetic acid, acetone, acetonitrile, anisole, benzene, 1-butanol, 2-butanol, n-butyl acetate, methyl tert-butyl ether, carbon tetrachloride, chlorobenzene, chloroform, cumene, cyclohexane, 1,2-dichloroethane, 1,1-dichloroethylene, 1,2-dichloroethylene, dichloromethane, 1,2-dimethoxyethane, N,N-dimethylacetamide, N,N-dimethylformamide, dimethyl sulfoxide, 1,4-dioxane, ethanol, 2-ethoxyethanol, ethyl acetate, ethylene glycol, diethyl ether, ethyl formate, formamide, formic acid, n-heptane, n-hexane, isobutyl acetate, isopropyl acetate, methanol, 2-methoxyethanol, methyl acetate, 3-methyl-1-butanol, methyl butyl ketone, methylcyclohexane, methyl ethyl ketone, methyl isobutyl ketone, isobutyl alcohol, N-methyl-2-pyrrolidone, nitromethane, n-pentane, 1-pentanol, 1-propanol, isopropyl alcohol, n-propyl acetate, pyridine, sulfolane, tetrahydrofuran, 1,2,3,4-tetrahydronaphthalene, toluene, 1,1,1-trichloroethane, trichloroethylene, m-xylene, water, triethylamine, and 1-octanol.

9. The method as recited in claim 4, wherein:
    the reference hydrophobicity solvent is hexane;
    the reference solvation solvent is dimethyl sulfoxide;
    the reference polarity solvent is nitromethane; and
    the reference hydrophilicity solvent is water.

10. The method as recited in claim 4, wherein the sigma profile for the molecule is generated using a coefficient vector defined by:

$$p_I(\sigma)A_I = A_{ref}[X, Y^-, Y^+, Z]^T$$

where $A_I$ is a surface area of a spherical cavity which enshrouds the molecule, $A_{ref}$ is a matrix generated from the sigma profile vector of the reference hydrophobicity solvent, the reference solvation solvent, the reference polarity solvent and the reference hydrophilicity solvent, and $]X, Y^-, Y^+, Z[^T$ is a coefficient vector of hydrophobicity (X), solvation ($Y^-$), polarity ($Y^+$) and hydrophilicity (Z) at a specific temperature (T).

11. The method as recited in claim 1, wherein the step of receiving the sigma profile for the molecule comprises obtaining the sigma profile from a database.

12. The method as recited in claim 1, wherein the step of receiving the sigma profile for the molecule comprises generating the sigma profile for the molecule using a vapor-liquid equilibrium data for a reference hydrophobicity solvent, a reference solvation solvent, a reference polarity solvent and a reference hydrophilicity solvent.

13. The method as recited in claim 1, wherein the activity coefficient for the molecule in the solvent is represented by:

$$\ln \gamma_{I/S} = n_I \sum_{\sigma_m} p_I(\sigma_m)[\ln \Gamma_S(\sigma_m) - \ln \Gamma_I(\sigma_m)] + \ln \gamma_{I/S}^{SG}$$

where $\ln \gamma_{I/S}$ is a natural logarithm of the activity coefficient for the molecule, the molecule is divided into a number of segments $n_I$ having a fixed surface area, $\sigma_m$ is a charge density of a segment m, $p_I(\sigma_m)$ is the generated sigma profile for the molecule, $\ln \Gamma_I(\sigma_m)$ is a natural logarithm of a segment activity coefficient for the molecule, $\ln \Gamma_S(\sigma_m)$ is a natural logarithm of a segment activity coefficient for a mixture of the molecule and a solvent, and $\ln \gamma_{I/S}^{SG}$ is a natural logarithm of a Staverman-Guggenheim activity coefficient.

14. The method as recited in claim 1, wherein the solubility of the molecule is represented by:

$$\ln x_I^{sat} \gamma_I^{sat} = \frac{\Delta H_{fus}}{R}\left(\frac{1}{T_m} - \frac{1}{T}\right)$$

where $\ln x_I^{sat} \gamma_I^{sat}$ is a natural logarithm of the solubility and calculated activity coefficient of the molecule, $\Delta H_{fus}$ is a enthalpy of fusion, R is a universal gas constant, $T_m$ is a melting temperature, and T is a specific temperature.

15. The method as recited in claim 1, wherein the solubility of the molecule is represented by:

$$\ln x_I^{sat} \gamma_I^{sat} = \ln K_{sp}$$

where $\ln x_I^{sat} \gamma_I^{sat}$ is a natural logarithm of the solubility and calculated activity coefficient of the molecule, and $\ln K_{sp}$ is a natural logarithm of an adjustable parameter regressed from an experimental solubility data for the molecule.

16. The method as recited in claim 15, further comprising the step of calculating the adjustable parameter from the experimental solubility data for the molecule using a regression analysis.

17. The method as recited in claim 1, further comprising the step of using the sigma profile in a conductor like screening model.

18. A computerized method for generating a sigma profile for a molecule comprising the steps of:
providing a processor, a memory communicably coupled to the processor and an output device communicably coupled to the processor;
generating the sigma profile for hie molecule using the processor and a set of sigma profile vectors for a reference hydrophobicity solvent, a reference solvation solvent, a reference polarity solvent and a reference hydrophilicity solvent;
(a) calculating an activity coefficient for the molecule using the sigma profile for the molecule using the processor;
(b) calculating a solubility for the molecule using the activity coefficient for the molecule using the processor;
(c) determining whether the sigma profile has converged using an objective function and one or more constraints to minimize an error between the calculated solubility for the molecule and an experimental solubility for the molecule using the processor, wherein the objective function and the one or more constraints are represented by:

$$\underset{XY^-Y^+Z}{minimize} \frac{1}{n}\sum_j^n [\ln x_j^{exp} - \ln x_j^{calc}]^2$$

subject to $$p_I(\sigma) \geq 0$$

where $X, Y^-, Y^+, Z$ is a coefficient vector of hydrophobicity (X), solvation ($Y^-$), polarity ($Y^+$) and hydrophilicity (Z), n is number of data points, $x_j^{exp}$ is the experimental solubility of the molecule, $\ln x_j^{calc}$ is calculated solubility of the molecule, $p_I(\sigma)$ is the generated sigma profile for the molecule;
whenever the sigma profile has not converged, adjusting the sigma profile for the molecule using the objective function sand the one or more constraints and repeating steps (a) through (c) using the processor,
whenever the sigma profile has converged, providing the sigma profile to the output device; and
developing a chemical process or product using the optimized sigma profile.

19. The method as recited in claim 18, wherein the sigma profile converges when a change in the sigma profile is less than or equal to a threshold value, the change in the sigma profile increases, or a maximum number of iterations have been completed.

20. The method as recited in claim 18, wherein the sigma profile is generated without any identification of a molecular structure of the molecule.

21. The method as recited in claim 18, wherein the sigma profile is generated without using any density functional theory (DFT) calculations or quantum mechanics calculations.

22. The method as recited in claim 18, further comprising the steps of:
selecting the reference hydrophobicity solvent, the reference solvation solvent, the reference polarity solvent and the reference hydrophilicity solvent; and obtaining the set of sigma profile vectors of the reference hydrophobicity solvent, the reference solvation solvent, the reference polarity solvent and the reference hydrophilicity solvent.

23. The method as recited in claim 22, wherein the reference hydrophobicity solvent, the reference solvation solvent, the reference polarity solvent and the reference hydrophilicity solvent are selected from the group consisting essentially acetic acid, acetone, acetonitrile, anisole, benzene, 1-butanol, 2-butanol, n-butyl acetate, methyl tert-butyl ether, carbon tetrachloride, chlorobenzene, chloroform, cumene, cyclohexane, 1,2-dichloroethane, 1,1-dichloroethylene, 1,2-dichloroethylene, dichloromethane, 1,2-dimethoxyethane, N,N-dimethylacetamide, N,N-dimethylformamide, dimethyl sulfoxide, 1,4-dioxane, ethanol, 2-ethoxyethanol, ethyl acetate, ethylene glycol, diethyl ether, ethyl formate, formamide, formic acid, n-heptane, n-hexane, isobutyl acetate, isopropyl acetate, methanol, 2-methoxyethanol, methyl acetate, 3-methyl-1-butanol, methyl butyl ketone, methylcyclohexane, methyl ethyl ketone, methyl isobutyl ketone, isobutyl alcohol, N-methyl-2-pyrrolidone, nitromethane, n-pentane, 1-pentanol, 1-propanol, isopropyl alcohol, n-propyl acetate, pyridine, sulfolane, tetrahydrofuran, 1,2,3,4-tetrahydronaphthalene, toluene, 1,1,1-trichloroethane, trichloroethylene, m-xylene, water, triethylamine, and 1-octanol.

24. The method as recited in claim 18, wherein:
the reference hydrophobicity solvent is hexane;
the reference solvation solvent is dimethyl sulfoxide;
the reference polarity solvent is nitromethane; and
the reference hydrophilicity solvent is water.

25. The method as recited in claim 18, wherein the sigma profile for the molecule is generated using a coefficient vector defined by:

$$p_I(\sigma)A_I = A_{ref}[X, Y^-, Y^+, Z]^T$$

where $A_I$ is a surface area of a spherical cavity which enshrouds the molecule, $A_{ref}$ is a matrix generated from the sigma profile vector of the reference hydrophobicity solvent, the reference solvation solvent, the reference polarity solvent and the reference hydrophilicity solvent, and $[X, Y^-, Y^+, Z]^T$ is a coefficient vector of hydrophobicity (X), solvation ($Y^-$), polarity ($Y^+$) and hydrophilicity (Z) at a specific temperature (T).

26. The method as recited in claim 18, wherein the activity coefficient for the molecule in the solvent is represented by:

$$\ln \gamma_{I/S} = n_I \sum_{\sigma_m} p_I(\sigma_m)[\ln \Gamma_S(\sigma_m) - \ln \Gamma_I(\sigma_m)] + \ln \gamma_{I/S}^{SG}$$

where $\ln \gamma_{I/S}$ is a natural logarithm of the activity coefficient for the molecule, the molecule is divided into a number of segments $n_I$ having a fixed surface area, $\sigma_m$ is a charge density of a segment m, $p_I(\sigma_m)$ is the generated sigma profile for the molecule, $\ln \Gamma_I(\sigma_m)$ is a natural logarithm of a segment activity coefficient for the molecule, $\ln \Gamma_S(\sigma_m)$ is a natural logarithm of a segment activity coefficient for a mixture of the molecule and a solvent, and $\ln \gamma_{I/S}^{SG}$ is a natural logarithm of a Staverman-Guggenheim activity coefficient.

27. The method as recited in claim 18, wherein the solubility of the molecule is represented by:

$$\ln x_I^{sat} \gamma_I^{sat} = \frac{\Delta H_{fus}}{R}\left(\frac{1}{T_m} - \frac{1}{T}\right)$$

where $\ln x_I^{sat} \gamma_I^{sat}$ is a natural logarithm of the solubility and calculated activity coefficient of the molecule, $\Delta H_{fus}$ is a enthalpy of fusion, R is a universal gas constant, $T_m$ is a melting temperature, and T is a specific temperature.

28. The method as recited in claim 18, wherein the solubility of the molecule is represented by:

$$\ln x_I^{sat} \gamma_I^{sat} = \ln K_{sp}$$

where $\ln x_I^{sat} \gamma_I^{sat}$ is a natural logarithm of the solubility and calculated activity coefficient of the molecule, and $\ln K_{sp}$ is a natural logarithm of an adjustable parameter regressed from an experimental solubility data for the molecule.

29. The method as recited in claim 28, further comprising the step of calculating the adjustable parameter from the experimental solubility data for the molecule using a regression analysis.

30. The method as recited in claim 18, further comprising the step of using the sigma profile in a conductor like screening model.

31. A computerized method for generating a sigma profile for a molecule comprising the steps of:
providing a processor, a memory communicably coupled to the processor and an output device communicably coupled to the processor;
selecting a reference hydrophobicity solvent, a reference solvation solvent, a reference polarity solvent and a reference hydrophilicity solvent;
obtaining a set of sigma profile vectors of the reference hydrophobicity solvent, the reference solvation solvent, the reference polarity solvent and the reference hydrophilicity solvent;
generating the sigma profile for the molecule using a coefficient vector defined by:

$$p_I(\sigma)A_I = A_{ref}[X, Y^-, Y^+, Z]^T$$

where $A_I$ is a surface area of a spherical cavity which enshrouds the molecule, $A_{ref}$ is a matrix generated from the sigma profile vector of the reference hydrophobicity solvent, the reference solvation solvent, the reference polarity solvent and the reference hydrophilicity solvent, and $[X, Y^-, Y^+, Z]^T$ is a coefficient vector of hydrophobicity (X), solvation ($Y^-$), polarity ($Y^+$) and hydrophilicity (Z) at a specific temperature (T);

(a) calculating an activity coefficient for the molecule using the sigma profile for the molecule using the processor wherein the activity coefficient is represented by:

$$\ln \gamma_{I/S} = n_I \sum_{\sigma_m} p_I(\sigma_m)[\ln \Gamma_S(\sigma_m) - \ln \Gamma_I(\sigma_m)] + \ln \gamma_{I/S}^{SG}$$

where $\ln \gamma_{I/S}$ is a natural logarithm of the activity coefficient for the molecule, the molecule is divided into a number of segments $n_I$ having a fixed surface area, $\sigma_m$ is a charge density of a segment m, $p_I(\sigma_m)$ is the generated sigma profile for the molecule, $\ln \Gamma_I(\sigma_m)$ is a natural logarithm of a segment activity coefficient for the molecule, $\ln \Gamma_S(\sigma_m)$ is a natural logarithm of a segment activity coefficient for a mixture of the molecule and a solvent, and $\ln \gamma_{I/S}^{SG}$ is a natural logarithm of a Staverman-Guggenheim activity coefficient;

(b) calculating a solubility for the molecule using the activity coefficient for the molecule using the processor;

(c) determining whether the sigma profile has converged using an objective function and one or more constraints using the processor wherein the objective function and the one or more constraints are represented by:

$$\underset{XY^-Y^+Z}{\text{minimize}} \frac{1}{n} \sum_{j}^{n} [\ln x_j^{exp} - \ln x_j^{calc}]^2$$

subject to $$p_I(\sigma) \geq 0$$

where n is number of data points, $x_j^{exp}$ is an experimental solubility of the molecule, $\ln x_j^{calc}$ is the calculated solubility of the molecule, and $p_I(\sigma)$ is the generated sigma profile for the molecule;

whenever the sigma profile has not converged, adjusting the sigma profile for the molecule using the objective function and the one or more constraints and repeating steps (a) through (c) using the processor;

whenever the sigma profile has converged, providing the sigma profile to the output device; and developing a chemical process or product using the optimized sigma profile.

32. The method as recited in claim 31, wherein the sigma profile converges when a change in the sigma profile is less than or equal to a threshold value, the change in the sigma profile increases, or a maximum number of iterations have been completed.

33. The method as recited in claim 31, wherein the sigma profile is generated without any identification of a molecular structure of the molecule.

34. The method as recited in claim 31, wherein the sigma profile is generated without using any density functional theory (DFT) calculations or quantum mechanics calculations.

35. The method as recited in claim 31, wherein the reference hydrophobicity solvent, the reference solvation solvent, the reference polarity solvent and the reference hydrophilicity solvent are selected from the group consisting essentially acetic acid, acetone, acetonitrile, anisole, benzene, 1-butanol, 2-butanol, n-butyl acetate, methyl tert-butyl ether, carbon tetrachloride, chlorobenzene, chloroform, cumene, cyclohexane, 1,2-dichloroethane, 1,1-dichloroethylene, 1,2-dichloroethylene, dichloromethane, 1,2-dimethoxyethane, N,N-dimethylacetamide, N,N-dimethylformamide, dimethyl sulfoxide, 1,4-dioxane, ethanol, 2-ethoxyethanol, ethyl acetate, ethylene glycol, diethyl ether, ethyl formate, formamide, formic acid, n-heptane, n-hexane, isobutyl acetate, isopropyl acetate, methanol, 2-methoxyethanol, methyl acetate, 3-methyl-1-butanol, methyl butyl ketone, methylcyclohexane, methyl ethyl ketone, methyl isobutyl ketone, isobutyl alcohol, N-methyl-2-pyrrolidone, nitromethane, n-pentane, 1-pentanol, 1-propanol, isopropyl alcohol, n-propyl acetate, pyridine, sulfolane, tetrahydrofuran, 1,2,3,4-tetrahydronaphthalene, toluene, 1,1,1-trichloroethane, trichloroethylene, m-xylene, water, triethylamine, and 1-octanol.

36. The method as recited in claim 31, wherein:
the reference hydrophobicity solvent is hexane;
the reference solvation solvent is dimethyl sulfoxide;
the reference polarity solvent is nitromethane; and
the reference hydrophilicity solvent is water.

37. The method as recited in claim 31, wherein the solubility of the molecule is represented by:

$$\ln x_I^{sat} \gamma_I^{sat} = \frac{\Delta H_{fus}}{R} \left( \frac{1}{T_m} - \frac{1}{T} \right)$$

where $\ln x_I^{sat} \gamma_I^{sat}$ is a natural logarithm of the solubility and calculated activity coefficient of the molecule, $\Delta H_{fus}$ is a enthalpy of fusion, R is a universal gas constant, $T_m$ is a melting temperature, and T is a specific temperature.

38. The method as recited in claim 31, wherein the solubility of the molecule is represented by:

$$\ln x_I^{sat} \gamma_I^{sat} = \ln K_{sp}$$

where $\ln x_I^{sat} \gamma_I^{sat}$ is a natural logarithm of the solubility and calculated activity coefficient of the molecule, and $\ln K_{sp}$ is a natural logarithm of an adjustable parameter regressed from an experimental solubility data for the molecule.

39. The method as recited in claim 38, further comprising the step of calculating the adjustable parameter from the experimental solubility data for the molecule using a regression analysis.

40. The method as recited in claim 31, wherein the objective function and the one or more constraints minimize an error between the calculated solubility for the molecule and an experimental solubility for the molecule.

41. The method as recited in claim 31, further comprising the step of using the sigma profile in a conductor like screening model.

42. A non-transitory computer readable medium encoded with a computer program for execution by a processor for optimizing a sigma profile for a molecule, the computer program comprising:

receiving the sigma profile for the molecule;
calculating an activity coefficient for the molecule using the sigma profile for the molecule using the processor;
calculating a solubility for the molecule using the activity coefficient for the molecule using the processor;
optimizing the sigma profile for the molecule by adjusting the sigma profile using an objective function and one or more constraints to minimize an error between the calculated solubility for the molecule and an experimental solubility for the molecule using the processor, wherein the objective function and the one or more constraints are represented by:

$$\underset{XY^-Y^+Z}{\text{minimize}} \frac{1}{n} \sum_{j}^{n} [\ln x_j^{exp} - \ln x_j^{calc}]^2$$

subject to $$p_I(\sigma) \geq 0$$

where X, $Y^-$, $Y^+$, Z is a coefficient vector of hydrophobicity (X), solvation ($Y^-$), polarity ($Y^+$) and hydrophilicity (Z), n is number of data points, $x_j^{exp}$ is the experimental solubility of the molecule, $\ln x_j^{calc}$ is calculated solubility of the molecule, $p_I(\sigma)$ is the generated sigma profile for the molecule;

providing the sigma profile to an output device communicably coupled to the processor; and developing a chemical process or product using the optimized sigma profile.

43. An apparatus for optimizing a sigma profile for a molecule comprising:

a processor, a memory communicably coupled to the processor;

an output device communicably coupled to the processor;

a non-transitory computer readable medium encoded with a computer program for execution by the processor that causes the processor to calculate an activity coefficient for the molecule using the sigma profile for the molecule, calculate a solubility for the molecule using the activity coefficient for the molecule, optimize the sigma profile for the molecule by adjusting the sigma profile using an objective function and one or more constraints to minimize an error between the calculate solubility for the molecule and an experimental solubility for the molecule, wherein the objective function and the one or more constraints are represented by:

$$\underset{XY^-Y^+Z}{minimize} \frac{1}{n}\sum_{j}^{n}[\ln x_j^{exp} - \ln x_j^{calc}]^2$$

subject to $$p_I(\sigma) \geq 0$$

where X, Y⁻, Y⁺, Z is a coefficient vector of hydrophobicity (X), solvation (Y⁻), polarity (Y⁺) and hydrophilicity (Z), n is number of data points, $x_j^{exp}$ is the experimental solubility of the molecule, ln $x_j^{calc}$ is calculated solubility of the molecule, $p_I(\sigma)$ is the generated sigma profile for the molecule, and provide the sigma profile to the output device; and wherein the optimized sigma profile is used to develop a chemical process or product.

44. A non-transitory computer readable medium encoded with a computer program fir execution by a processor for generating a sigma profile for a molecule, the computer program comprising:

generating the sigma profile for the molecule using a set of sigma profile vectors for a reference hydrophobicity solvent, a reference solvation solvent, a reference polarity solvent and a reference hydrophilicity solvent;

(a) calculating an activity coefficient for the molecule using the sigma profile far the molecule;

(b) calculating a solubility for the molecule using the activity coefficient for the molecule;

(c) determining whether the sigma profile has converged using an objective function and one or more constraints to minimize an error between the calculated solubility for the molecule and an experimental solubility for the molecule, wherein the objective function and the one more constraints are represented by:

$$\underset{XY^-Y^+Z}{minimize} \frac{1}{n}\sum_{j}^{n}[\ln x_j^{exp} - \ln x_j^{calc}]^2$$

subject to $$p_I(\sigma) \geq 0$$

where X, Y⁻, Y⁺, Z is a coefficient vector of hydrophobicity (X), solvation (Y⁻), polarity (Y⁺) and hydrophilicity (Z), n is number of data points, $x_j^{exp}$ is the experimental solubility of the molecule, ln $x_j^{calc}$ is calculated solubility of the molecule, $p_I(\sigma)$ is the generated sigma profile for the molecule;

whenever the sigma profile has not converged, adjusting the sigma profile for the molecule using the objective function and the one or more constraints and repeating steps (a) through (c);

whenever the sigma profile has converged, providing the sigma profile to an output device communicably coupled to the processor; and wherein the optimized sigma profile is used to develop a chemical process or product.

45. An apparatus for generating a sigma profile for a molecule comprising:

a processor, a memory communicably coupled to the processor;

an output device communicably coupled to the processor;

a non-transitory computer readable medium encoded with a computer program for execution by the processor that cause the processor to generate the sigma profile for the molecule using a set of sigma profile vectors for a reference hydrophobicity solvent, a reference solvation solvent, a reference, polarity solvent and a reference hydrophilicity solvent, (a) calculate an activity coefficient for the molecule using the sigma profile for the molecule, (b) calculate a solubility for the molecule using the activity coefficient for the molecule, (c) determine whether the sigma profile has converged using an objective function and one or more constraints to minimize an error between the calculated solubility for the molecule and an experimental solubility for the molecule, wherein the objective function and the one or more constraints are represented by:

$$\underset{XY^-Y^+Z}{minimize} \frac{1}{n}\sum_{j}^{n}[\ln x_j^{exp} - \ln x_j^{calc}]^2$$

subject to $$p_I(\sigma) \geq 0$$

where X, Y⁻, Y⁺, Z is a coefficient vector of hydrophobicity (X), solvation (Y⁻), polarity (Y⁺) and hydrophilicity (Z), n is number of data points, $x_j^{exp}$ is the experimental solubility of the molecule, ln $x_j^{calc}$ is calculated solubility of the molecule, $p_I(\sigma)$ is the generated sigma profile for the molecule, whenever the sigma profile has not converged, adjusting the sigma profile for the molecule using the objective function and the one or more constraints and repeating steps (a) through (c), whenever the sigma profile has converged, providing the sigma profile to an output device communicably coupled to the processor; and wherein the optimized sigma profile is used to develop a chemical process or product.

46. A non-transitory computer readable medium encoded with a computer program for execution by a processor for generating a sigma profile for a molecule, the computer program comprising:

selecting a reference hydrophobicity solvent, a reference solvation solvent, a reference polarity solvent and a reference hydrophilicity solvent;

obtaining a set of sigma profile vectors of the reference hydrophobicity solvent, the reference solvation solvent, the reference polarity solvent and the reference hydrophilicity solvent;

generating the sigma profile for the molecule using a coefficient vector defined by:

$$p_I(\sigma)A_I = A_{ref}[X,Y^-,Y^+,Z]^T$$

where $A_I$ is a surface area of a spherical cavity which enshrouds the molecule, $A_{ref}$ is a matrix generated from the sigma profile vector of the reference hydrophobicity solvent, the reference solvation solvent, the reference polarity solvent and the reference hydrophilicity solvent, and $[X, Y^-, Y^+, Z]^T$ is a coefficient vector of hydrophobicity (X), solvation ($Y^-$), polarity ($Y^+$) and hydrophilicity (Z) at a specific temperature (T);

(a) calculating an activity coefficient for the molecule using the sigma profile for the molecule using the processor wherein the activity coefficient is represented by:

$$\ln \gamma_{I/S} = n_I \sum_{\sigma_m} p_I(\sigma_m)[\ln \Gamma_S(\sigma_m) - \ln \Gamma_I(\sigma_m)] + \ln \gamma_{I/S}^{SG}$$

where $\ln \gamma_{I/S}$ is a natural logarithm of the activity coefficient for the molecule, the molecule is divided into a number of segments $n_I$ having a fixed surface area, $\sigma_m$ is a charge density of a segment m, $p_I(\sigma_m)$ is the generated sigma profile for the molecule, $\ln \Gamma_I(\sigma_m)$ is a natural logarithm of a segment activity coefficient for the molecule, $\ln \Gamma_S(\sigma_m)$ is a natural logarithm of a segment activity coefficient for a mixture of the molecule and a solvent, and $\ln \gamma_{I/S}^{SG}$ is a natural logarithm of a Staverman-Guggenheim activity coefficient;

(b) calculating a solubility for the molecule using the activity coefficient for the molecule;
(c) determining whether the sigma profile has converged using an objective function and one or more constraints wherein the objective function and the one or more constraints are represented by:

$$\underset{XY^-Y^+Z}{minimize} \frac{1}{n} \sum_{j}^{n} [\ln x_j^{exp} - \ln x_j^{calc}]^2$$

subject to $$p_I(\sigma) \geq 0$$

where n is number of data points, $x_j^{exp}$ is an experimental solubility of the molecule, $\ln x_j^{calc}$ is the calculated solubility of the molecule, and $p_I(\sigma)$ is the generated sigma profile for the molecule;
whenever the sigma profile has not converged, adjusting the sigma profile for the molecule using the objective function and the one or more constraints and repeating steps (a) through (c);
whenever the sigma profile has converged, providing the sigma profile to an output device communicably coupled to the processor; and
wherein the optimized sigma profile is used to develop a chemical process or product.

47. An apparatus for generating a sigma profile for a molecule comprising:
a processor;
a memory communicably coupled to the processor;
an output device communicably coupled to the processor;
a non-transitory computer readable medium encoded with a computer program for execution by the processor that causes the processor to (1) select a reference hydrophobicity solvent, a reference solvation solvent, a reference polarity solvent and a reference hydrophilicity solvent, (2) obtain a set of sigma profile vectors of the reference hydrophobicity solvent, the reference solvation solvent, the reference polarity solvent and the reference hydrophilicity solvent, (3) generate the sigma profile for the molecule using a coefficient vector defined by:

$$p_I(\sigma)A_I = A_{ref}[X,Y^-,Y^+,Z]^T$$

where $A_I$ is a surface area of a spherical cavity which enshrouds the molecule, $A_{ref}$ is a matrix generated from the sigma profile vector of the reference hydrophobicity solvent, the reference solvation solvent, the reference polarity solvent and the reference hydrophilicity solvent, and $[X, Y^-, Y^+, Z]^T$ is a coefficient vector of hydrophobicity (X), solvation ($Y^-$), polarity ($Y^+$) and hydrophilicity (Z) at a specific temperature (T);

(a) calculating an activity coefficient for the molecule using the sigma profile for the molecule using the processor wherein the activity coefficient is represented by:

$$\ln \gamma_{I/S} = n_I \sum_{\sigma_m} p_I(\sigma_m)[\ln \Gamma_S(\sigma_m) - \ln \Gamma_I(\sigma_m)] + \ln \gamma_{I/S}^{SG}$$

where $\ln \gamma_{I/S}$ is a natural logarithm of the activity coefficient for the molecule, the molecule is divided into a number of segments $n_I$ having a fixed surface area, $\sigma_m$ is a charge density of a segment m, $p_I(\sigma_m)$ is the generated sigma profile for the molecule, $\ln \Gamma_I(\sigma_m)$ is a natural logarithm of a segment activity coefficient for the molecule, $\ln \Gamma_S(\sigma_m)$ is a natural logarithm of a segment activity coefficient for a mixture of the molecule and a solvent, and $\ln \gamma_{I/S}^{SG}$ is a natural logarithm of a Staverman-Guggenheim activity coefficient, (b) calculate a solubility for the molecule using the activity coefficient for the molecule,
(c) determine whether the sigma profile has converged using an objective function and one or more constraints wherein the objective function and the one or more constraints are represented by:

$$\underset{XY^-Y^+Z}{minimize} \frac{1}{n} \sum_{j}^{n} [\ln x_j^{exp} - \ln x_j^{calc}]^2$$

subject to $$p_I(\sigma) \geq 0$$

where n is number of data points, $x_j^{exp}$ is an experimental solubility of the molecule, $\ln x_j^{calc}$ is the calculated solubility of the molecule, and $p_I(\sigma)$ is the generated sigma profile for the molecule, (4) whenever the sigma profile has not converged, adjust the sigma profile for the molecule using the objective function and the one or more constraints and repeating steps (a) through (c), and (5) whenever the sigma profile has converged, provide the sigma profile to an output device communicably coupled to the processor; and
wherein the optimized sigma profile is used to develop a chemical process or product.

* * * * *